US011229658B2

(12) United States Patent
Sprenger et al.

(10) Patent No.: US 11,229,658 B2
(45) Date of Patent: Jan. 25, 2022

(54) COMPOSITIONS FOR USE IN THE PREVENTION OR TREATMENT OF OTITIS OR BRONCHITIS IN INFANTS OR YOUNG CHILDREN

(71) Applicant: NESTEC S.A., Vevey (CH)

(72) Inventors: Norbert Sprenger, Savigny (CH); Dominique Brassart, Chavannes-pres-Renens (CH); Delphine Egli, La Tour-de-Peilz (CH)

(73) Assignee: Societe des Produits Nestle S.A., Vevey (CH)

( * ) Notice: Subject to any disclaimer, the term of this patent is extended or adjusted under 35 U.S.C. 154(b) by 68 days.

(21) Appl. No.: 15/555,168

(22) PCT Filed: Mar. 4, 2016

(86) PCT No.: PCT/EP2016/054612
§ 371 (c)(1),
(2) Date: Sep. 1, 2017

(87) PCT Pub. No.: WO2016/193928
PCT Pub. Date: Sep. 9, 2016

(65) Prior Publication Data
US 2018/0042949 A1    Feb. 15, 2018

(30) Foreign Application Priority Data
Mar. 5, 2015   (EP) .................................. 15157723

(51) Int. Cl.
| *A61K 31/702* | (2006.01) |
| *A61K 9/00* | (2006.01) |
| *A23L 33/00* | (2016.01) |
| *A23L 33/21* | (2016.01) |
| *A23L 33/125* | (2016.01) |
| *A61K 35/741* | (2015.01) |
| *A61K 35/00* | (2006.01) |

(52) U.S. Cl.
CPC .......... *A61K 31/702* (2013.01); *A23L 33/125* (2016.08); *A23L 33/21* (2016.08); *A23L 33/30* (2016.08); *A23L 33/40* (2016.08); *A61K 9/0056* (2013.01); *A61K 9/0095* (2013.01); *A61K 35/741* (2013.01); *A23V 2002/00* (2013.01); *A23V 2200/314* (2013.01); *A61K 2035/115* (2013.01)

(58) Field of Classification Search
CPC .. A61K 31/702; A61K 9/0056; A61K 9/0095; A61K 35/741; A61K 2035/115; A23L 33/21; A23L 33/30; A23L 33/125; A23L 33/40; A23L 33/19; A23L 33/26; A23L 33/115; A23L 33/16; A23L 33/15; A23L 33/135; A23L 33/155; A23L 33/00; A23V 2200/314; A23V 2002/00; A61P 27/16; A61P 11/00

See application file for complete search history.

(56) References Cited

U.S. PATENT DOCUMENTS

| 6,146,670 | A | * | 11/2000 | Prieto | ..................... | A23L 29/30 |
| | | | | | | 426/580 |
| 2009/0220639 | A1 | * | 9/2009 | Schmitt | .................... | A23L 33/12 |
| | | | | | | 426/2 |
| 2012/0171166 | A1 | | 7/2012 | Chow et al. | | |
| 2012/0172319 | A1 | | 7/2012 | Chow et al. | | |
| 2012/0172330 | A1 | | 7/2012 | Buck et al. | | |
| 2012/0172331 | A1 | | 7/2012 | Buck et al. | | |
| 2012/0177691 | A1 | | 7/2012 | Stahl et al. | | |
| 2013/0236424 | A1 | * | 9/2013 | Sprenger | .................. | A23L 33/40 |
| | | | | | | 424/93.4 |
| 2015/0031645 | A1 | | 1/2015 | Buck et al. | | |

FOREIGN PATENT DOCUMENTS

| EP | 2522232 A1 * | 11/2012 | ............... C07H 5/06 |
| WO | WO-2009060073 A1 * | 5/2009 | ......... A61K 31/7028 |

OTHER PUBLICATIONS

Victoria State Government Health and Human Services/Better Health Channel (Year: 2014).*
NY Health Department, Ear Infections in Children (Year: 2012).*
Whitney et al. "Lower respiratory tract infections: prevention using vaccines" Infect Dis Clin N Am 18 (2004), 899-917. (Year: 2004).*
Medical Microbiology, 4th Edition Chapter 93 "Infections of the Respiratory System" Dasaraja et al. (Year: 1996).*
Bode, Lars "Human milk oligosaccharides: Every baby needs a sugar mama" Glycobiology, 2012, vol. 22, No. 9, pp. 1147-1162.
Sumiyoshi et al. "Determination of each neutral oligosaccharide in the milk of Japanese women during the course of lactation" British Journal of Nutrition, 2003, vol. 89, pp. 61-69.
Office Action received for Russian Patent Application No. 2017133815, dated Sep. 5, 2019, 18 pages. (6 pages of English Translation and 12 pages of official copy).

* cited by examiner

*Primary Examiner* — Marcia S Noble
*Assistant Examiner* — Lauren K Van Buren
(74) *Attorney, Agent, or Firm* — K&L Gates LLP

(57) ABSTRACT

The present invention relates to a nutritional composition comprising at least one fucosylated oligosaccharide and at least one N-acetylated oligosaccharide in particular amounts, for use in preventing and/or treating infections and/or inflammations of the lower respiratory tract and/or of the ear in an infant or a young child.

7 Claims, 6 Drawing Sheets

Bronchitis

Figure 1A:
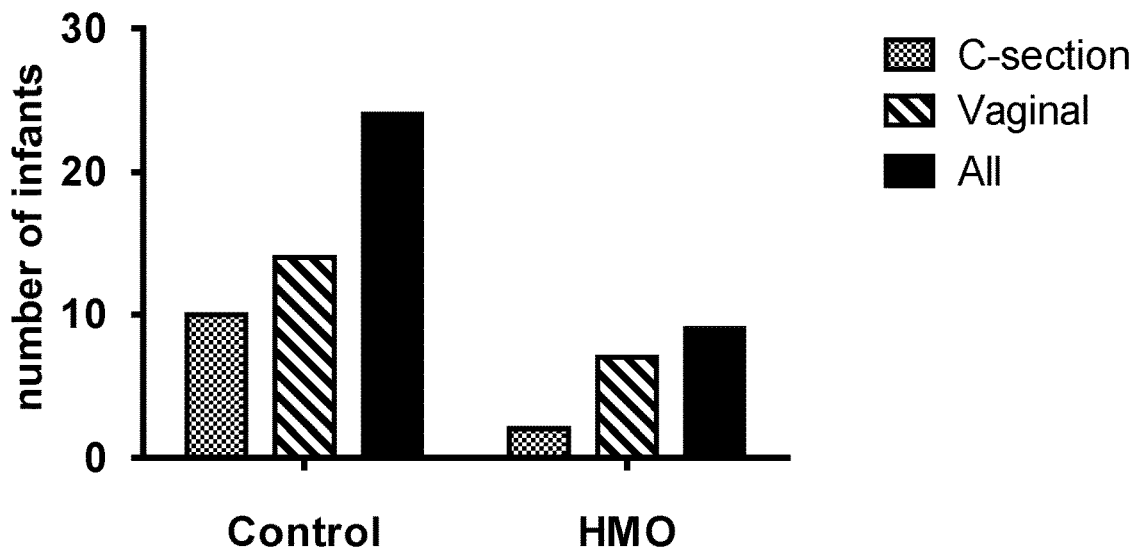

COMPOSITIONS FOR USE IN THE PREVENTION OR TREATMENT OF OTITIS OR BRONCHITIS IN INFANTS OR YOUNG CHILDREN

CROSS REFERENCE TO RELATED APPLICATIONS

The present application is a National Stage of International Application No. PCT/EP2016/054612, filed on Mar. 4, 2016, which claims priority to European Patent Application No. 15157723.6, filed on Mar. 5, 2015, the entire contents of which are being incorporated herein by reference.

FIELD OF THE INVENTION

This invention relates to compositions for use in preventing and/or treating infections and/or inflammations of the lower respiratory tract and/or of the ear, such as bronchitis or otitis, in infants or young children.

BACKGROUND OF THE INVENTION

Infections and/or inflammations of the respiratory tract are very common, especially in infants and young children because of their weak conditions and immature immune defences (e.g. their respiratory tract is not yet strong in fighting off these infections and/or inflammations). For example, in the first year of life, an infant will often experience from three to six of such infections. These infections and/or inflammations may have a bacterial origin, a viral origin, or an environmental origin.

The infections of the respiratory tract can affect various parts of the respiratory tract of the infants and young children. There may be upper respiratory tract infections (also called URT infections or URTI) that are illnesses caused by an acute infection involving the upper respiratory tract (i.e. upper airways): nose, sinuses, pharynx and/or larynx. The most common examples of URT infections are rhinitis, rhinosinusitis, nasopharyngitis, pharyngitis, epiglottitis, laryngitis, tonsillitis, laryngotracheitis, tracheitis, or combinations thereof. URTI are often caused by viruses. Over 200 different viruses have been isolated in patients with URIs. The most common virus is called the rhinovirus. Other viruses include the coronavirus, parainfluenza virus, adenovirus, enterovirus, and respiratory syncytial virus.

The other type of respiratory tract infections is called the lower respiratory tract infections (also called LRT infections or LRTI). These are illnesses caused by an acute infection involving the lower respiratory tract (i.e. lower airways): trachea, bronchi, bronchioles and/or lungs. Examples of infections of the lower respiratory tract include pneumonia, bronchitis, bronchiolitis.

LRTI may sometimes be preceded by a typical viral URTI.

LRT infections may be caused by bacteria or viruses. Some examples of responsible bacteria are *Streptococcus pneumoniae, Haemophilus influenzae, Moraxella catarrhalis, Staphylococcus aureus, Klebsiella pneumoniae*, anterobacteria such as *Escherichia coli*, anaerobes. Some examples of responsible virus are: Influenza A virus, respiratory syncytial virus (RSV), human metapneumovirus (hMPV), varicella-zoster virus.

The main symptoms of LRT infections are grunting, feeding difficulties, irritability, poor sleep, cough and/or tachypnoea. The LRT infections may also be accompanied by fever.

Most of the LRT infections used to be fatal, but with new research and medicine, they are now treatable. With bacterial infections, antibiotics are prescribed, while viral infections are harder to treat, but still curable. Antibiotics are often thought to be the first line treatment in lower respiratory tract infections; however, these are not indicated in viral infections. There are also issues regarding the emerging resistance of bacteria to the antibiotics treatments.

Some environmental factors may also be responsible of inflammations of the lower respiratory tract, e.g. pulmonary inflammations, such as smoke, chemical inhalation, air pollution (e.g. fossil fuel (diesel, coal) particles) and sand storms.

Infections and/or inflammations of the ear are also common in infants and young children. There may be from bacterial or viral origin. Some examples of infections and/or inflammations of the ear include ear infections, ear inflammations, otitis, otitis media, acute otitis media, otitis externa, mastoiditis, labyrinthitis. Otitis externa refers to an inflammation of the outer ear, mastoiditis refers to an inflammation of the mastoid and labyrinthitis refers to an inflammation of the inner ear. The most common example of infections and/or inflammations of the ear is otitis such as otitis media which is an inflammation of the middle ear. The otitis media may be: acute otitis media, otitis media with effusion, unresponsive acute otitis media, recurrent acute otitis media, otitis media with complications or chronic suppurative otitis media.

Otitis media may also be preceded by an URTI and/or by a LRTI (so an infant or young child may suffer from an infection/inflammation of both the lower respiratory tract and the ear). The main symptom of otitis media is ear pain, but it can also be accompanied of fever and/or irritability. This is an infection of the middle ear in which the Eustachian tube which connects the cavity of the middle ear with the external environment via the mouth becomes inflamed and then blocked trapping bacteria in the middle ear. The middle ear cavity also becomes inflamed with a build-up of fluid leading to increased pressure which is experienced by the patient as pain due to the inability to equalise pressure between the middle ear and the external environment via the Eustachian tube as in healthy subjects. In severe cases, the tympanic membrane may burst under pressure allowing the infected liquid to reach the inner ear. This is a potentially dangerous situation which can lead to permanently impaired hearing if left untreated. 50% of children have at least one episode of acute otitis media in the first year of life (i.e. as an infant), and 35% of children between one and three years of age (i.e. as a young child) have recurrent episodes of acute otitis media. This in turn may lead to the development of a condition called glue ear in which the fluid does not completely drain from the middle ear between bouts of infection. If this condition becomes established, surgical intervention may be necessary.

Acute otitis media appears to be mostly linked with the activity of pathogenic bacteria commonly found in the indigenous microbiota of the naso-pharyngeal cavity. Quantitatively, the most important pathogens are *Streptococcus pneumoniae* (35% of cases), untypeable *Haemophilus influenzae* (30% of cases) and *Moraxella catarrhalis* (10% of cases). For this reason, acute otitis media is commonly treated by the administration of antibiotics especially in infants. Indeed, antibiotics are prescribed more frequently for treatment of otitis media than for any other illness in infancy. This has also inevitably led to the development of resistance to the commonly prescribed antibiotics in the bacterial strains associated with otitis media. For example, it is thought that at least 20% of *S. pneumoniae* strains are resistant to penicillins and cephalosporins. Similarly, at least 30% of *H. influenzae* strains and the majority of *M. catarrhalis* strains have developed antibiotic resistance. This frequency of prescription is at least in part due to the pain experienced by infants and young children suffering from otitis media to which they react by prolonged crying which parents and other care givers are very anxious to relieve. Otitis might also be caused by viruses such as RSV and common cold causing rhino virus. In this case antibiotic treatments would not be efficient.

There is thus clearly a need for alternative methods to decrease the incidence of these painful and potentially serious health conditions in infants and young children.

Many attempts have been made to develop alternative pathways to prevent/treat infections and/or inflammations of the lower respiratory tract and of the ear. The use of probiotics has especially been investigated. Probiotics are considered to be viable microbial preparations which promote the individual's health by preserving the natural microflora in the intestine. Probiotics are deemed to attach to the intestine's mucosa, colonize the intestinal tract and likewise prevent attachment of harmful microorganisms thereon. A crucial prerequisite for their action resides in that they have to reach the gut's mucosa in a proper and viable form and do not get destroyed in the upper part of the gastrointestinal tract, especially by the influence of the low pH prevailing in the stomach.

For example WO2008042101 from Danisco provides methods for reducing respiratory disease in children, comprising: providing a culture of *L. acidophilus*; providing a child at risk of developing respiratory disease; and administering the culture of *L. acidophilus* to the child at risk, under conditions such that the risk of developing respiratory disease is reduced. However, adding live probiotic bacteria to products so that they remain viable until consumption is a non-trivial task. In particular for products with longer storage times this is difficult to accomplish and may require additional technical efforts. This invention targets children who are preferably from 3 to 5 years old.

Other routes than probiotics have been explored such as the use of oligosaccharides, and especially human milk oligosaccharides. Human milk oligosaccharides (HMOs) are, collectively, the third largest solid constituents in human milk, after lactose and fat. HMOs usually consist of lactose at the reducing end with a carbohydrate core that often contains a fucose or a sialic acid at the non-reducing end. There are over one hundred milk oligosaccharides that have been isolated and characterized in human milk.

Mother's milk is recommended for all infants. However, in some cases breast feeding is inadequate or unsuccessful for medical reasons or the mother chooses not to breast feed. Infant formulae have been developed for these situations. Fortifiers have also been developed to enrich mother's milk or infant formula with specific ingredients.

Several compositions have therefore been developed using HMO ingredients, such as fucosylated oligosaccharides, lacto-N-tetraose, lacto-N-neotetraose and/or sialylated oligosaccharides, and for different purposes.

For example WO2005055944 from Children's hospital medical center describes a pharmaceutical composition comprising a molecule comprising a fucose group in an alpha-2 linkage, an alpha-3 linkage or an alpha-4 linkage to a galactose group and a pharmaceutically acceptable carrier. Various molecules are described such as 2'-fucosyllactose. This application is quite general since several infections can be prevented or treated, including respiratory or enteric infections, and there is a large target of patients (infants, children or adults).

WO2012092158 from Abbott refers to a pediatric formula comprising a mixture of sialylated oligosaccharides in specific amounts for modulating respiratory virus-induced inflammation.

WO2009/059996 and WO2012/076323 from Nestec SA disclose compositions with mixture of HMOs comprising necessarily sialylated oligosaccharides as essential components for the prevention of secondary infections or acute respiratory infections (ARI).

Further studies were specifically focused on various associations of HMOs with either a probiotic strain or with other specific components.

For example WO2009/077352 from Nestec SA relates to a composition suitable in the prevention of opportunistic infections comprising a particular synergistic association of a probiotic *Bifidobacterium* with a fucosylated oligosaccharide. Respiratory tracts infections are cited amongst the opportunistic infections that may be prevented. This invention especially targets immune-compromised individuals such as preterm infants, older children or adults with an immune system which is not fully effective as a result of an existing condition or illness (e.g. HIV) or as a result of therapy for an existing condition e.g. Crohn's disease or rheumatoid arthritis or chemo-therapy for the treatment of cancer).

Oligosaccharides in general are known for their general protective role on gastrointestinal, respiratory or urinary tract, see for example Wataru et al, 2003 and in WO9843494. However most of these studies describe various HMOs without associating a particular type of oligosaccharides or synergic associations thereof to a particular benefit. They also describe various examples of concentrations, and they only refer to general benefits (e.g. not focused on lower respiratory tract and ear).

WO2012/092154 from Abbott refers to methods of using HMOs for improving airway respiratory health of infants, toddlers and children. However a wide list of HMOs is indicated in this application as well as several combinations of different HMOs. It is claimed that the composition seems to be efficient only when HMOs are present with carotenoid.

WO2012092155 describe compositions comprising HMOs with necessarily another type of prebiotic selected from the list of GOS or FOS, and targeting benefits from the gastrointestinal tract.

Several other studies also refer to the treatment/prevention of pathogenic infections of the URT, which is different to the LRT since they affect/involve other tissues/body parts, as previously explained. For example WO2009/112361 from Nestec SA relates to another composition suitable in the prevention of opportunistic infections comprising a particular synergistic association of a N-acetyl-lactosamine and/or an oligosaccharide containing N-acetyl-lactosamine with a probiotic *Lactobacillus* sp. Several conditions are cited such as pathogenic infections of the upper respiratory tract.

None of the previous work is therefore focused on the prevention and/or treatment of infections/inflammations of the lower respiratory tract and of the ear in infants or young children whereas they have higher risks of developing these infections/inflammations than the average.

There is clearly a need for developing suitable methods to decrease the incidence of these health conditions in infants and young children.

There is also a need to deliver such health benefits in a manner that is particularly suitable for the young subjects (infants and young children), in a manner that does not involve a classical pharmaceutical intervention as these infants or young children are particularly fragile.

There is a need to deliver such health benefits in these infants or young children in a manner that does not induce side effects and/or in a manner that is easy to deliver, and well accepted by the parents or health care practitioners.

There is also a need to deliver such benefits in a manner that does keep the cost of such delivery reasonable and affordable by most.

There is thus clearly a need to develop alternative methods than the classical pharmaceutical intervention such as the use of antibiotics, at least because of the previously mentioned issues of resistance development.

There is also a need to develop an alternative treatment pathway that may be efficient for a broad range of origins, i.e. independently of the causes of the infections and/or inflammations (e.g. bacterial, viral or environmental origins).

SUMMARY OF THE INVENTION

The present inventors have found that a composition comprising at least one fucosylated oligosaccharide and at least one N-acetylated oligosaccharide, both in a particular amount, can advantageously be used against infections and/or inflammations of the lower respiratory tract such as bronchitis, but also the infections and/or inflammations of the ear such as otitis, in an infant or a young child. Without wishing to be bound by theory it is believed that these oligosaccharide(s) act synergically for these specific health conditions.

Accordingly, the present invention therefore provides a nutritional composition comprising at least one fucosylated oligosaccharide and at least one N-acetylated oligosaccharide, for use in preventing and/or treating infections and/or inflammations of the lower respiratory tract and/or of the ear in an infant or a young child, wherein
  the fucosylated oligosaccharide(s) is/are in a total amount of 0.75-1.65 g/L of the composition and/or in a total amount of 0.52-1.15 g/100 g of composition on a dry weight basis; and
  the N-acetylated oligosaccharide(s) is/are in a total amount of 0.45-0.85 g/L of the composition and/or in a total amount of 0.31-0.59 g/100 g of composition on a dry weight basis.

In a particularly advantageous embodiment, the nutritional composition comprises 2'-fucosyllactose (2-FL) and lacto-N-neotetraose (LNnT), and especially 2'-fucosyllactose (2-FL) in an amount of 1-1.5 g/L of the nutritional composition and LNnT in an amount of 0.5-0.7 g/L of the nutritional composition.

The present inventors have also found that the particular nutritional composition according to the invention is particularly efficient in reducing fever and the use (i.e. administration) of antibiotics and the use of antipyretics in an infant or a young child.

FIGURES

FIG. 1 represent the number of infants having at least one bronchitis episode, said infants fed either a standard infant formula (Control group) or a standard formula supplemented with 1.24 g/L of 2'-fucosyllactose and 0.63 g/L lacto-N-neotetraose (HMO group). In C-section born infants OR=0.15, p=0.02; In vaginal born infants OR=0.42, p=0.095; In all infants together OR=0.3, p=0.004. In Control group n=87 and in HMO group n=88.

FIG. 1A: partial results (not all infants' data were received), within the first 12 months of birth.

Figure 1B:
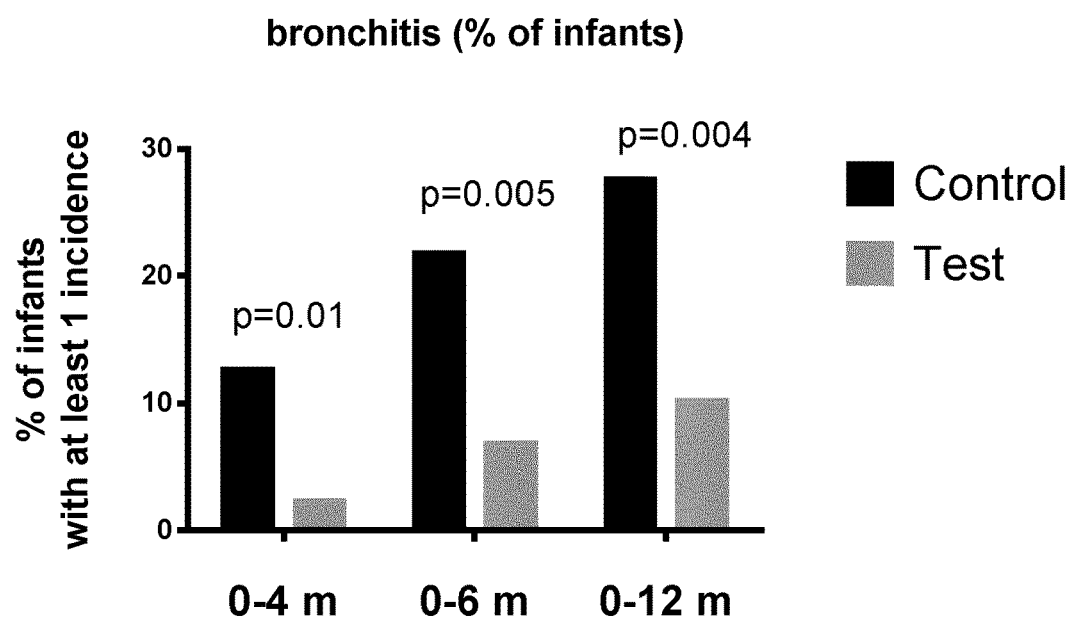

FIG. 1B: total results (all infants' data were received), data from 0-4, 0-6 and 0-12 months of birth.

FIG. 2 represent the number of infants having at least one episode of ear infections/inflammations within the first 12 months of birth, said infants fed either a standard infant formula (Control group) or a standard formula supplemented with 1.24 g/L of 2'-fucosyllactose and 0.63 g/L lacto-N-neotetraose (HMO group). In all infants together OR=0.3, p=0.06. In control n=87, in HMO group n=88.

Figure 2A:
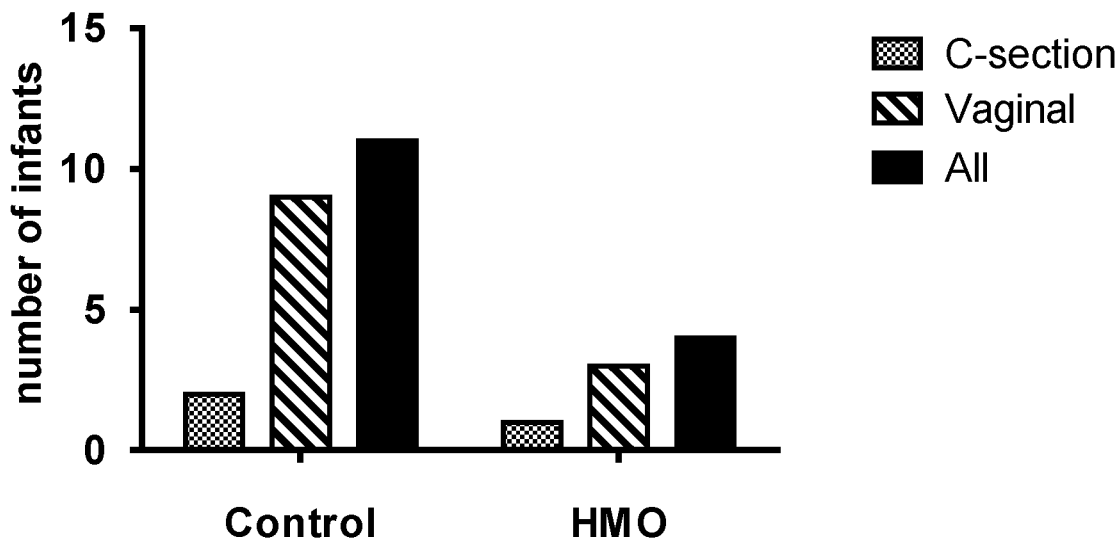

FIG. 2A: partial results (not all infants' data were received), within the first 12 months of birth.

Figure 2B:
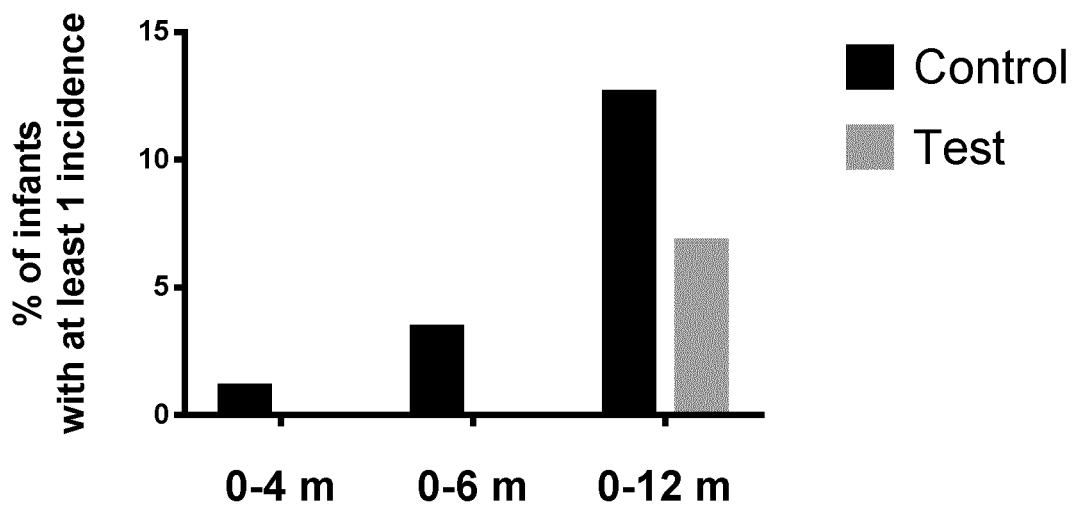

FIG. 2B: total results (all infants' data were received), data from 0-4, 0-6 and 0-12 months of birth.

FIG. 3 represent the number of infants who were administered antibiotics at least once within the first 12 months of birth, said infants fed either a standard infant formula (Control group) or a standard formula supplemented with 1.24 g/L of 2'-fucosyllactose and 0.63 g/L lacto-N-neotetraose (HMO group). In C-section born infants OR=0.5, p=0.2; In vaginal born infants OR=0.45, p=0.068; In all infants together OR=0.47, p=0.025. In Control group n=87, in HMO group n=88.

Figure 3A:
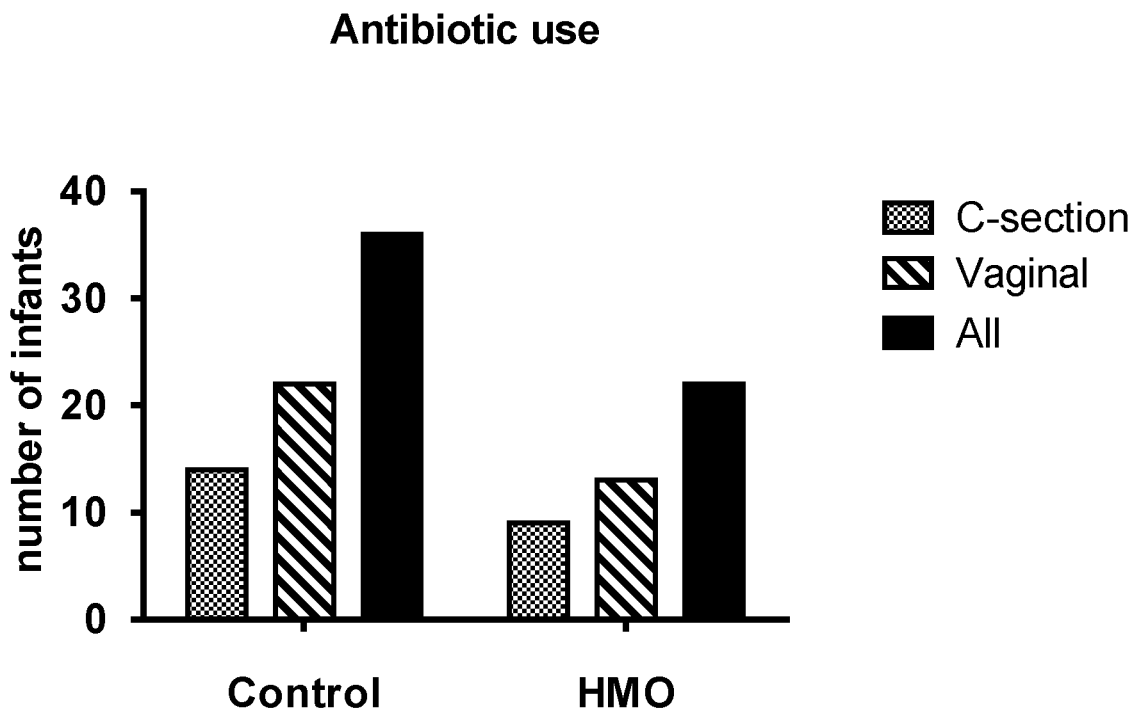

FIG. 3A: partial results (not all infants' data were received), within the first 12 months of birth.

Figure 3B:
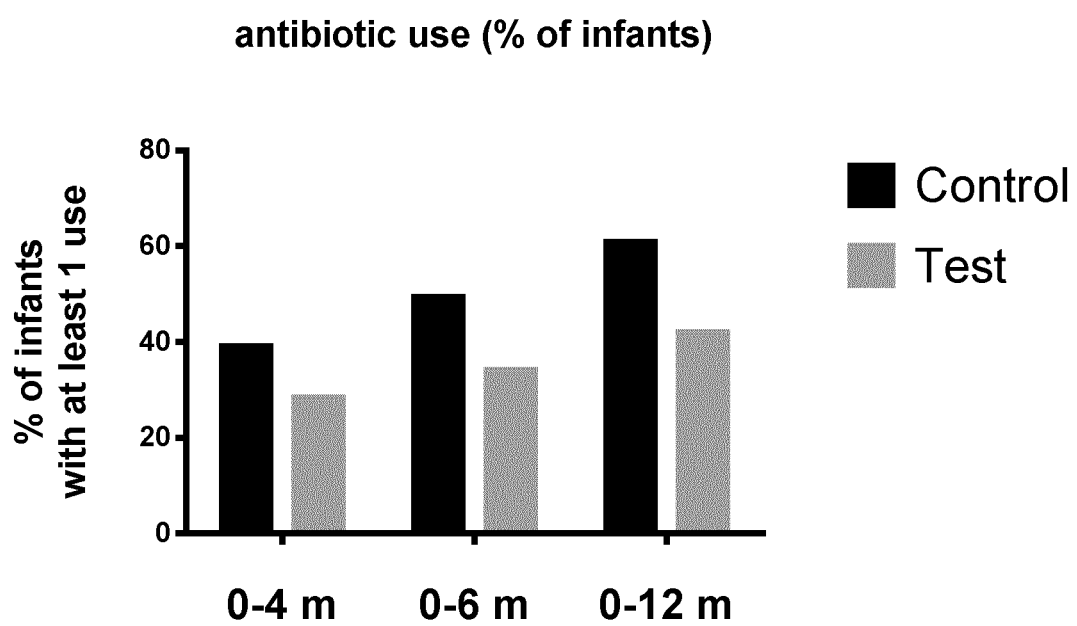

FIG. 3B: total results (all infants' data were received), data from 0-4, 0-6 and 0-12 months of birth.

FIG. 4 represent the number of infants who had at least one episode of fever within the first 12 months of birth, said infants fed either a standard infant formula (Control group) or a standard formula supplemented with 1.24 g/L of 2'-fucosyllactose and 0.63 g/L lacto-N-neotetraose (HMO group). In C-section born infants OR=0.3, p=0.6; In vaginal born infants OR=0.4, p=0.15; In all infants together OR=0.4, p=0.08. In Control group n=87, in HMO group n=88.

Figure 4A:
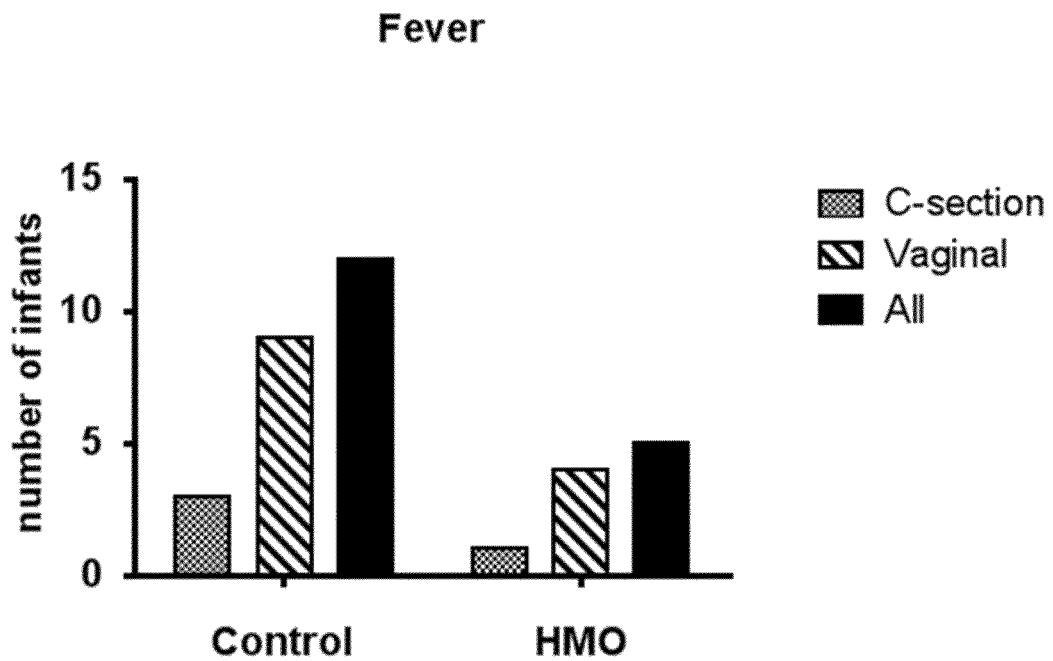

FIG. 4A: partial results (not all infants' data were received), within the first 12 months of birth.

Figure 4B:
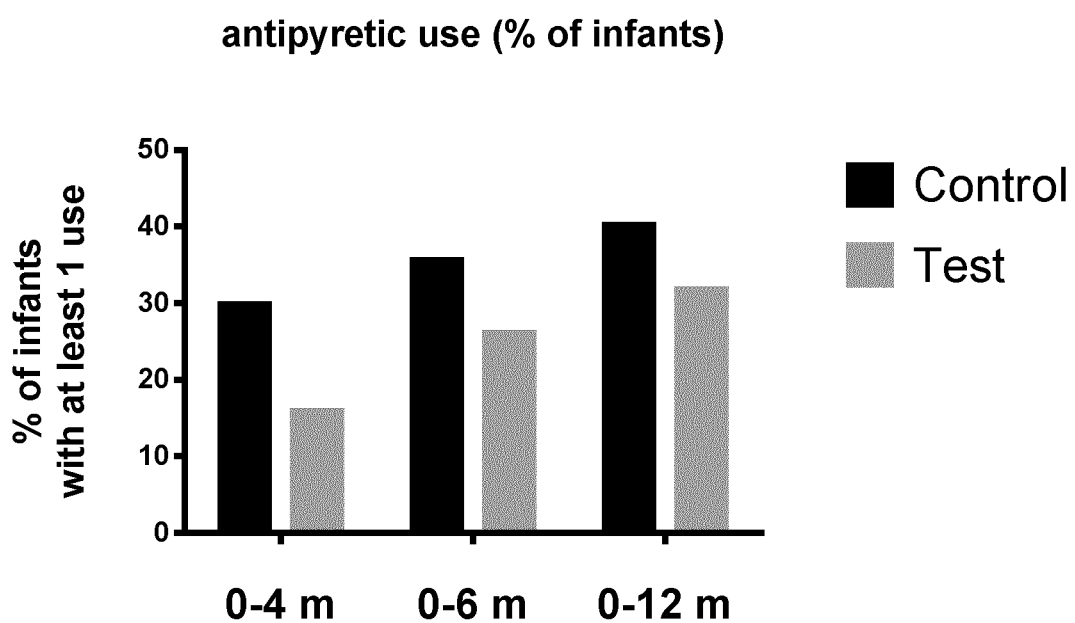

FIG. 4B: total results (all infants' data were received), data from 0-4, 0-6 and 0-12 months of birth.

Figure 5:
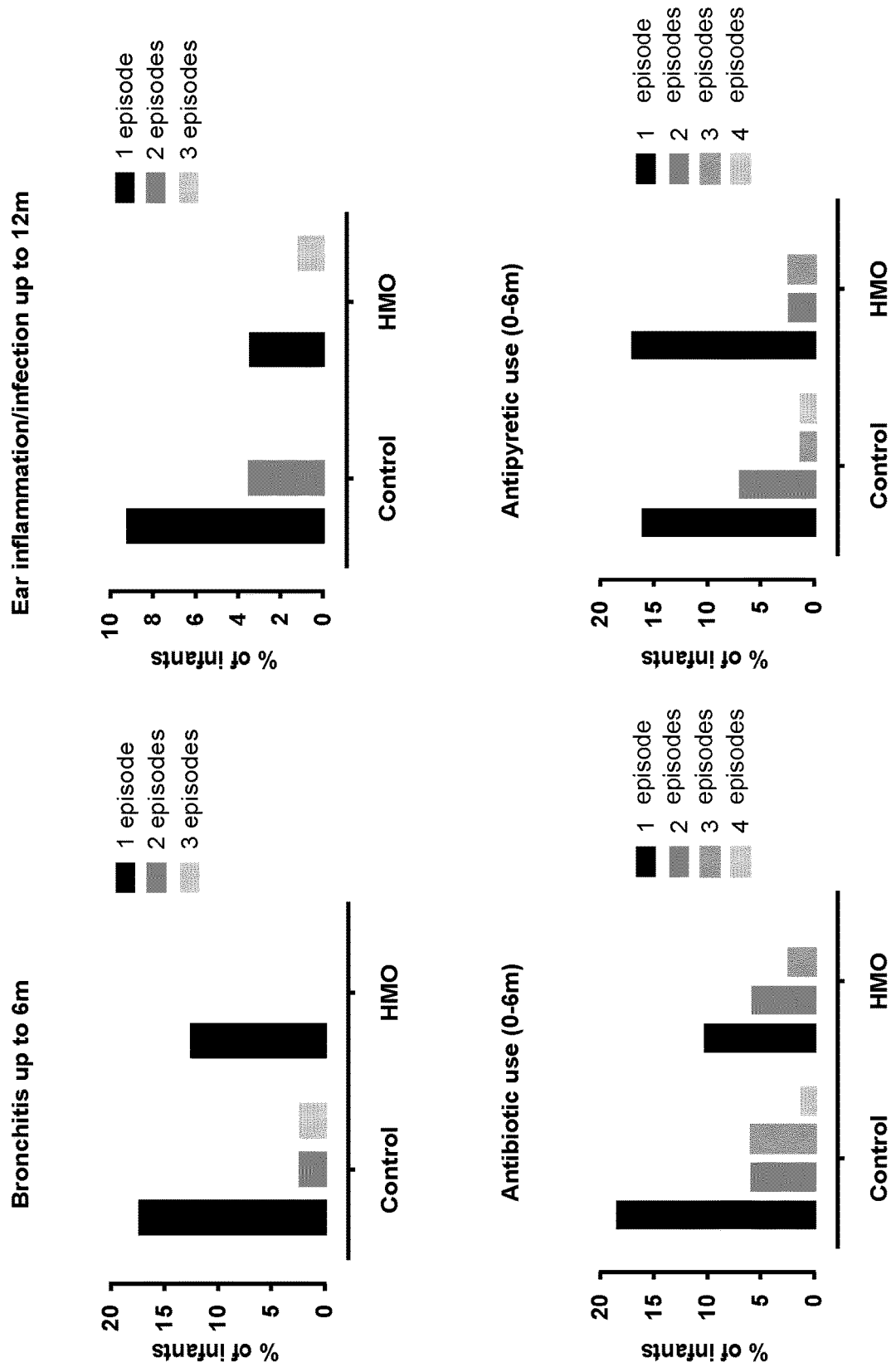

FIG. 5 depict the total number of events per group of bronchitis from 0-6 months of birth (FIG. 5A), ear infection/inflammation from 0-12 months of birth (FIG. 5B), antibiotic use from 0-6 months of birth (FIG. 5C) and antipyretic use from 0-6 months of birth (FIG. 5D), in infants fed either a standard infant formula (Control group) or a standard formula supplemented with 1.24 g/L of 2'-fucosyllactose and 0.63 g/L lacto-N-neotetraose (HMO group) (partial results—not all infants' data were received). Antibiotics encompass all prescribed medications having the capacity to inhibit the growth of or to kill microorganisms. Antipyretics encompass all prescribed medications having the capacity and aiming to reduce fever.

Figure 6:
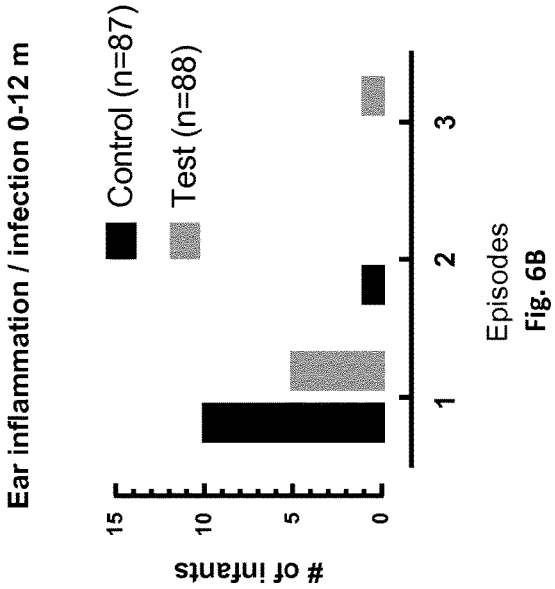
Figure 6:
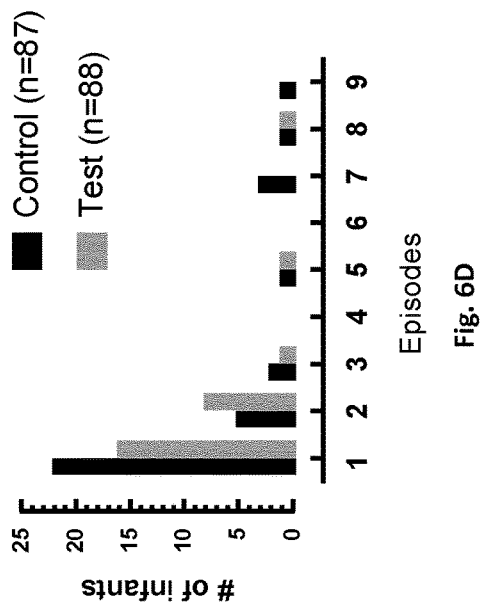
Figure 6:
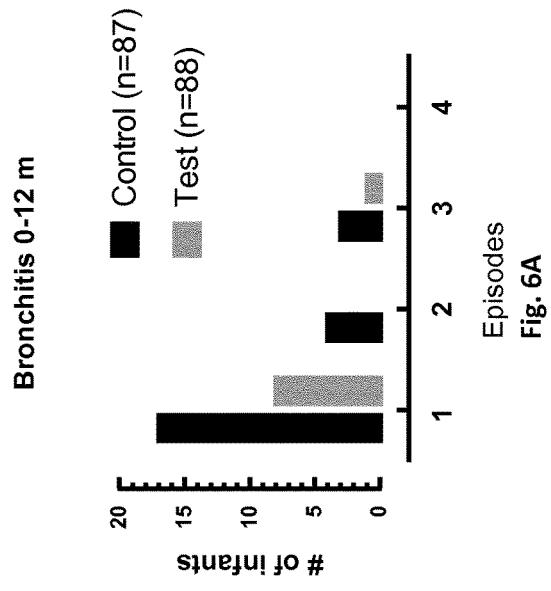
Figure 6:
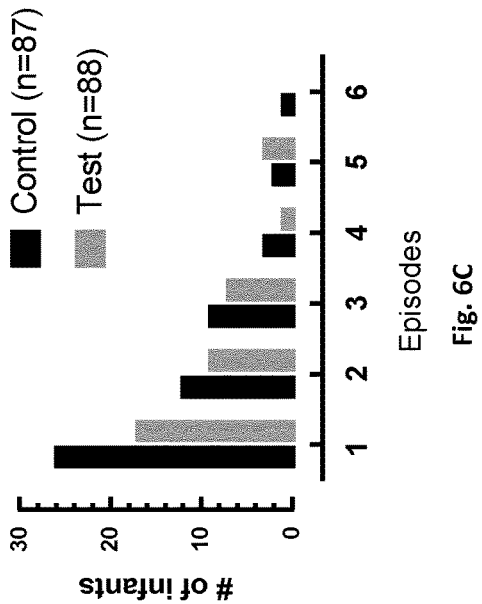

FIG. 6 depict the total number of events per group of bronchitis (FIG. 6A), ear infection/inflammation (FIG. 6B), antibiotic use (FIG. 6C) and antipyretic use (FIG. 6D), from 0-12 months of birth in infants fed either a standard infant formula (Control group) or a standard formula supplemented with 1.24 g/L of 2'-fucosyllactose and 0.63 g/L lacto-N-neotetraose (HMO group). Total results (all infants' data were received). The symbol # means number.

DETAILED DESCRIPTION OF THE INVENTION

As used herein, the following terms have the following meanings.

The term "infant" means a child under the age of 12 months.

The expression "young child" means a child aged between one and three years, also called toddler.

An "infant or young child born by C-section" means an infant or young child who was delivered by caesarean. It means that the infant or young child was not vaginally delivered.

An "infant or young child vaginally born" means an infant or young child who was vaginally delivered and not delivered by caesarean.

A "preterm" or "premature" means an infant or young child who was not born at term. Generally it refers to an infant or young child born prior 36 weeks of gestation.

The expression "nutritional composition" means a composition which nourishes a subject. This nutritional composition is usually to be taken orally or intravenously, and it usually includes a lipid or fat source and a protein source.

In a particular embodiment the composition of the present invention is a hypoallergenic nutritional composition. The expression "hypoallergenic nutritional composition" means a nutritional composition which is unlikely to cause allergic reactions.

In a particular embodiment the composition of the present invention is a "synthetic nutritional composition". The expression "synthetic nutritional composition" means a mixture obtained by chemical and/or biological means, which can be chemically identical to the mixture naturally occurring in mammalian milks (i.e. the synthetic composition is not breast milk).

The expression "infant formula" as used herein refers to a foodstuff intended for particular nutritional use by infants during the first months of life and satisfying by itself the nutritional requirements of this category of person (Article 2(c) of the European Commission Directive 91/321/EEC 2006/141/EC of 22 Dec. 2006 on infant formulae and follow-on formulae). It also refers to a nutritional composition intended for infants and as defined in Codex Alimentarius (Codex STAN 72-1981) and Infant Specialities (incl. Food for Special Medical Purpose). The expression "infant formula" encompasses both "starter infant formula" and "follow-up formula" or "follow-on formula".

A "follow-up formula" or "follow-on formula" is given from the 6th month onwards. It constitutes the principal liquid element in the progressively diversified diet of this category of person.

The expression "baby food" means a foodstuff intended for particular nutritional use by infants or young children during the first years of life.

The expression "infant cereal composition" means a foodstuff intended for particular nutritional use by infants or young children during the first years of life.

The term "fortifier" refers to liquid or solid nutritional compositions suitable for mixing with breast milk or infant formula.

The expression "weaning period" means the period during which the mother's milk is substituted by other food in the diet of an infant or young child.

The expressions "days/weeks/months/years of life" and "days/weeks/months/years of birth" can be used interchangeably.

The expression "preventing and/or treating infections and/or inflammations of the lower respiratory tract and/or of the ear" encompasses one or several of the following:
preventing infections of the lower respiratory tract
preventing infections of the ear
preventing inflammations of the lower respiratory tract
preventing inflammation of the ear
treating infections of the lower respiratory tract
treating infections of the ear
treating inflammations of the lower respiratory tract
treating inflammation of the ear The expressions "lower respiratory tract infections", "infections of the lower respiratory tract", "LRT infections" or "LRTI" can be used interchangeably. These are illnesses caused by an acute infection involving the lower respiratory tract (i.e. lower airways): trachea, bronchi, bronchioles and/or lungs. Examples of LRT infections are pneumonia, bronchitis, bronchiolitis or combinations thereof. The LRT infections may have a bacterial origin, a viral origin or an environmental origin, as previously detailed.

The expressions "infections and/or inflammations of the ear" and "ear infections and/or inflammations" can be used interchangeably. They include ear infections, ear inflammations, otitis, otitis media, acute otitis media, otitis externa, mastoiditis, labyrinthitis. Such infections and/or inflammations may have a bacterial origin, a viral origin or an environmental origin, as previously detailed.

The expressions "in preventing infections and/or inflammations", "to prevent infections and/or inflammations", "in the prevention of infections and/or inflammations" and "for the prevention of infections and/or inflammations" can be used interchangeably.

These expressions mean avoiding that infections and/or inflammations of the LRT/ear occur and/or decreasing the incidence of said infections and/or inflammations (reduction of the frequency, i.e. the number of LRT/ear infections and/or inflammations). In some embodiments the prevention of LRT/ear infections and/or inflammations occurs during the treatment (i.e. during the administration of the composition of the present invention, either immediately after the start of the administration or some time after, e.g. some days or weeks after the start). It can also encompass the prevention of LRT/ear infections and/or inflammations later in life. The term "later in life" encompasses the effect after the termination of the intervention or treatment. The effect "later in life" can be from 1 week to several months, for example from 2 to 4 weeks, from 2 to 6 weeks, from 2 to 8 weeks, from 1 to 6 months or from 2 to 12 months.

The expressions "in treating infections and/or inflammations", "to treat infections and/or inflammations", "in the treatment of infections and/or inflammations" and "for the treatment of infections and/or inflammations" can be used interchangeably. They should be understood as comprising the decrease of the duration of the LRT/ear infections and/or inflammations (number of days/weeks/years the infants or young children will suffer from LRT/ear infections and/or inflammations), of the severity of LRT/ear infections and/or inflammations (the consequences and/or the seriousness of LRT/ear infections and/or inflammations). These expressions also encompass the relieve of the symptoms such as grunting, feeding difficulties, irritability, poor sleep, cough, tachypnoea, ear pain, fever, and combinations thereof, and/or the decrease of complications caused by the LRT/ear infections and/or inflammations on the infant or young child health, such as asthma, glue ear issues, need of a surgical intervention, and/or the decrease of pain, and/or the decrease of tiredness, and/or the ease of the sleep and/or the stabilization of the activity of the infants or young children suffering from LRT/ear infections and/or inflammations.

The "mother's milk" should be understood as the breast milk or the colostrum of the mother.

An "oligosaccharide" is a saccharide polymer containing a small number (typically three to ten) of simple sugars (monosaccharides).

The term "HMO" or "HMOs" refers to human milk oligosaccharide(s). These carbohydrates are highly resistant to enzymatic hydrolysis, indicating that they may display essential functions not directly related to their caloric value. It has especially been illustrated that they play a vital role in the early development of infants and young children, such as the maturation of the immune system. Many different kinds of HMOs are found in the human milk. Each individual oligosaccharide is based on a combination of glucose, galactose, sialic acid (N-acetylneuraminic acid), fucose and/or N-acetylglucosamine with many and varied linkages between them, thus accounting for the enormous number of different oligosaccharides in human milk—over 130 such structures have been identified so far. Almost all of them have a lactose moiety at their reducing end while sialic acid and/or fucose (when present) occupy terminal positions at the non-reducing ends. The HMOs can be acidic (e.g. charged sialic acid containing oligosaccharide) or neutral (e.g. fucosylated oligosaccharide).

A "fucosylated oligosaccharide" is an oligosaccharide having a fucose residue. It has a neutral nature. Some examples are 2-FL (2'-fucosyllactose), 3-FL (3-fucosyllactose), difucosyllactose, lacto-N-fucopentaose (e.g. lacto-N-fucopentaose I, lacto-N-fucopentaose II, lacto-N-fucopentaose III, lacto-N-fucopentaose V), lacto-N-fucohexaose, lacto-N-difucohexaose I, fucosyllacto-N-hexaose, fucosyllacto-N-neohexaose, difucosyllacto-N-hexaose I, difucosyllacto-N-neohexaose II and any combination thereof. Without wishing to be bound by theory it is believed that the fucosyl-epitope of the fucosylated oligosaccharides may act as decoy at the mucosal surface. By a competition effect, it may prevent and/or limit the action of the pathogens responsible of infections (of viral or bacterial origin) or of their secreted components (e.g. toxins), especially by avoiding their binding to natural ligands, and without to be bound by theory, this is believed to therefore reduce the risk of infections/inflammations, and particularly the risk of LRT/ear infections and/or inflammations. In addition, the fucosylated oligosaccharides are thought to boost growth and metabolic activity of specific commensal microbes reducing inflammatory response and creating an environment unfavourable for pathogens thus leading to colonization resistance.

The expressions "fucosylated oligosaccharides comprising a 2'-fucosyl-epitope" and "2-fucosylated oligosaccharides" encompass fucosylated oligosaccharides with a certain homology of form since they contain a 2'-fucosyl-epitope, therefore a certain homology of function can be expected. Without wishing to be bound by theory the 2'-fucosyl-epitope of these fucosylated oligosaccharides is believed to be particularly specific to pathogens (or their secreted components) involved in the LRT and/or ear infections.

The expression "N-acetylated oligosaccharide(s)" encompasses both "N-acetyl-lactosamine" and "oligosaccharide(s) containing N-acetyl-lactosamine". They are neutral oligosaccharides having an N-acetyl-lactosamine residue. Suitable examples are LNT (lacto-N-tetraose), para-lacto-N-neohexaose (para-LNnH), LNnT (lacto-N-neotetraose) and any combinations thereof. Other examples are lacto-N-hexaose, lacto-N-neohexaose, para-lacto-N-hexaose, para-lacto-N-neohexaose, lacto-N-octaose, lacto-N-neooctaose, iso-lacto-N-octaose, para-lacto-N-octaose and lacto-N-decaose.

The expression "at least one fucosylated oligosaccharide" and "at least one N-acetylated oligosaccharide" means "at least one type of fucosylated oligosaccharide" and "at least one type of N-acetylated oligosaccharide".

A "precursor of HMO" is a key compound that intervenes in the manufacture of HMO, such as sialic acid and/or fucose.

A "sialylated oligosaccharide" is a charged sialic acid containing oligosaccharide, i.e. an oligosaccharide having a sialic acid residue. It has an acidic nature. Some examples are 3-SL (3' sialyllactose) and 6-SL (6' sialyllactose).

The nutritional composition of the present invention can be in solid form (e.g. powder) or in liquid form. The amount of the various ingredients (e.g. the oligosaccharides) can be expressed in g/100 g of composition on a dry weight basis when it is in a solid form, e.g. a powder, or as a concentration in g/L of the composition when it refers to a liquid form (this latter also encompasses liquid composition that may be obtained from a powder after reconstitution in a liquid such as milk, water . . . , e.g. a reconstituted infant formula or a follow-on/follow-up formula or an infant cereal product or any other formulation designed for infant nutrition).

The term "prebiotic" means non-digestible carbohydrates that beneficially affect the host by selectively stimulating the growth and/or the activity of healthy bacteria such as bifidobacteria in the colon of humans (Gibson G R, Roberfroid M B. *Dietary modulation of the human colonic microbiota: introducing the concept of prebiotics. J Nutr.* 1995; 125:1401-12).

The term "probiotic" means microbial cell preparations or components of microbial cells with a beneficial effect on the health or well-being of the host. (Salminen S, Ouwehand A. Benno Y. et al. "*Probiotics: how should they be defined*" Trends Food Sci. Technol. 1999:10 107-10). The microbial cells are generally bacteria or yeasts.

The term "cfu" should be understood as colony-forming unit.

All percentages are by weight unless otherwise stated.

In addition, in the context of the invention, the terms "comprising" or "comprises" do not exclude other possible elements. The composition of the present invention, including the many embodiments described herein, can comprise, consist of, or consist essentially of the essential elements and limitations of the invention described herein, as well as any additional or optional ingredients, components, or limitations described herein or otherwise depending on the needs.

Any reference to prior art documents in this specification is not to be considered an admission that such prior art is widely known or forms part of the common general knowledge in the field.

The invention will now be described in further details. It is noted that the various aspects, features, examples and embodiments described in the present application may be compatible and/or combined together.

A first object of the present invention is therefore a nutritional composition comprising at least one fucosylated oligosaccharide and at least one N-acetylated oligosaccharide, for use in preventing and/or treating infections and/or inflammations of the lower respiratory tract and/or of the ear in an infant or a young child, wherein the fucosylated oligosaccharide(s) is/are in a total amount of 0.75-1.65 g/L of the composition and/or in a total amount of 0.52-1.15 g/100 g of composition on a dry weight basis; and the N-acetylated oligosaccharide(s) is/are in a total amount of 0.45-0.85 g/L of the composition and/or in a total amount of 0.31-0.59 g/100 g of composition on a dry weight basis.

The composition of the present invention comprises at least one fucosylated oligosaccharide. There can be one or several types of fucosylated oligosaccharide(s). The fucosylated oligosaccharide(s) can indeed be selected from the list comprising 2'-fucosyllactose, 3' fucosyllactose, difucosyllactose, lacto-N-fucopentaose (such as lacto-N-fucopentaose I, lacto-N-fucopentaose II, lacto-N-fucopentaose III, lacto-N-fucopentaose V), lacto-N-fucohexaose, lacto-N-difucohexaose I, fucosyllacto-N-hexaose, fucosyllacto-N-neohexaose (such as fucosyllacto-N-neohexaose I, fucosyllacto-N-neohexaose II), difucosyllacto-N-hexaose I, difuco-lacto-N-neohexaose, difucosyllacto-N-neohexaose I, difucosyllacto-N-neohexaose II, fucosyl-para-Lacto-N-hexaose, tri-fuco-para-Lacto-N-hexaose I and any combination thereof.

In some particular embodiments the fucosylated oligosaccharide comprises a 2'-fucosyl-epitope. It can be for example selected from the list comprising 2'-fucosyllactose, difucosyllactose, lacto-N-fucopentaose, lacto-N-fucohexaose, lacto-N-difucohexaose, fucosyllacto-N-hexaose, fucosyllacto-N-neohexaose, difucosyllacto-N-hexaose difuco-lacto-N-neohexaose, difucosyllacto-N-neohexaose, fucosyl-para-Lacto-N-hexaose and any combination thereof.

In a preferred embodiment, the nutritional composition according to the invention comprises 2'-fucosyllactose (or 2FL, or 2'FL, or 2-FL or 2'-FL). In a particular embodiment, there is no other type of fucosylated oligosaccharide than 2'-fucosyllactose, i.e. the nutritional composition of the invention comprises only 2'-fucosyllactose as fucosylated oligosaccharide.

The fucosylated oligosaccharide(s) may be isolated by chromatography or filtration technology from a natural source such as animal milks. Alternatively, it may be produced by biotechnological means using specific fucosyltransferases and/or fucosidases either through the use of enzyme-based fermentation technology (recombinant or natural enzymes) or microbial fermentation technology. In the latter case, microbes may either express their natural enzymes and substrates or may be engineered to produce respective substrates and enzymes. Single microbial cultures and/or mixed cultures may be used. Fucosylated oligosaccharide formation can be initiated by acceptor substrates starting from any degree of polymerization (DP), from DP=1 onwards. Alternatively, fucosylated oligosaccharides may be produced by chemical synthesis from lactose and free fucose. Fucosylated oligosaccharides are also available for example from Kyowa, Hakko, Kogyo of Japan.

The composition of the present invention also comprises at least one the N-acetylated oligosaccharide. There can be one or several types of N-acetylated oligosaccharide.

The N-acetylated oligosaccharide(s) can be for example lacto-N-tetraose (LNT), lacto-N-neotetraose (LNnT) or any combination thereof. In some particular embodiments the N-acetylated oligosaccharide is lacto-N-neotetraose (LNnT), para-lacto-N-neohexaose (para-LNnH) or any combination thereof. In some particular embodiments the N-acetylated oligosaccharide is LNnT. In some particular embodiments the N-acetylated oligosaccharide is LNT. In some other particular embodiments the N-acetylated oligosaccharide is a mixture of LNT and LNnT. In some particular embodiments the composition comprises both LNT and LNnT in a ratio LNT:LNnT between 5:1 and 1:2, or from 2:1 to 1:1, or from 2:1.2 to 2:1.6.

In a preferred embodiment, the nutritional composition according to the invention comprises lacto-N-neotetraose (LNnT). In a particular embodiment, there is no other type of N-acetylated oligosaccharide than lacto-N-neotetraose (LNnT), i.e. the nutritional composition of the invention comprises only lacto-N-neotetraose (LNnT) as N-acetylated oligosaccharide.

The N-acetylated oligosaccharide(s) may be synthesised chemically by enzymatic transfer of saccharide units from donor moieties to acceptor moieties using glycosyltransferases as described for example in U.S. Pat. No. 5,288,637 and WO 96/10086. Alternatively, LNT and LNnT may be prepared by chemical conversion of Keto-hexoses (e.g. fructose) either free or bound to an oligosaccharide (e.g. lactulose) into N-acetylhexosamine or an N-acetylhexosamine-containing oligosaccharide as described in Wrodnigg, T. M.; Stutz, A. E. (1999) Angew. Chem. Int. Ed. 38:827-828. N-acetyl-lactosamine produced in this way may then be transferred to lactose as the acceptor moiety.

In a particularly advantageous embodiment of the present invention, the nutritional composition comprises 2'-fucosyllactose (2FL) and lacto-N-neotetraose (LNnT). In another specific embodiment, the nutritional composition of the present invention comprises an oligosaccharide mixture that consists of 2'-fucosyllactose (2-FL) and lacto-N-neotetraose (LNnT). In other words, the nutritional composition of the invention comprises only 2'-fucosyllactose (2-FL) as fucosylated oligosaccharide and only lacto-N-neotetraose (LNnT) as N-acetylated oligosaccharide.

In the present invention, the fucosylated oligosaccharide(s) and N-acetylated oligosaccharide(s) are present in the nutritional composition in some particular amounts. The term "amount" refers to the total amount of each of these 2 components in the nutritional composition unless otherwise specified. It therefore does not refer to an individual amount except when there is a single type of these components (in that case both the total and individual amounts equal). By way of illustrative example, if there is only one (i.e. only one type of) fucosylated oligosaccharide in the composition (e.g. 2FL), its individual amount (and therefore the total amount of fucosylated oligosaccharides) will be in the range 0.75-1.65 g/L. If there are several (i.e. several types of) fucosylated oligosaccharides, their individual amount will be lower (e.g. if there are 2 different types of fucosylated oligosaccharide, e.g. 2FL+3FL, there may be for example each in an individual amount of 0.5 g/L) but the total amount of fucosylated oligosaccharides will be in the range 0.75-1.65 g/L.

The fucosylated oligosaccharide(s) can be present in the nutritional composition according to the present invention in a total amount of 0.75-1.65 g/L of the composition. In some embodiments, the fucosylated oligosaccharide(s) may be in a total amount of 0.8-1.5 g/L of the composition, such as 0.85-1.3 g/L or 0.9-1.25 g/L or 0.9-1.1 g/L or 1-1.25 g/L or 1.05-1.25 g/L of the composition. In a particular embodiment, the fucosylated oligosaccharide(s) is/are in a total amount of 1 g/L of the composition. In another particular embodiment, the fucosylated oligosaccharide(s) is/are in a total amount of 1.24 g/L of the composition.

The fucosylated oligosaccharide(s) can be present in the nutritional composition in a total amount of 0.52-1.15 g/100 g of composition on a dry weight basis. The fucosylated oligosaccharide(s) may be in a total amount of 0.55-1.05 g/100 g of the composition, such as 0.59-0.9 g/100 g, or 0.62-0.87 g/100 g or 0.62-0.77 g/100 g or 0.69-0.87 g/100 g or 0.73-0.87 g/100 g of the composition. In a particular embodiment, the fucosylated oligosaccharide(s) is/are in a total amount of 0.69 g/100 g of the composition. In another particular embodiment, the fucosylated oligosaccharide(s) is/are in a total amount of 0.86 g/100 g of the composition.

The N-acetylated oligosaccharide(s) can be present in the nutritional composition according to the present invention in a total amount of 0.45-0.85 g/L of the composition. In some embodiments, the N-acetylated oligosaccharide(s) may be in a total amount of 0.5-0.8 g/L of the composition, such as 0.5-0.75 g/L or 0.5-0.7 g/L of the composition.

In a particular embodiment, the N-acetylated oligosaccharide(s) is/are in a total amount of 0.5 g/L of the composition. In another particular embodiment, the N-acetylated oligosaccharide(s) is/are in a total amount of 0.63 g/L of the composition.

The N-acetylated oligosaccharide(s) can be present in the nutritional composition in a total amount of 0.31-0.59 g/100 g of composition on a dry weight basis, The N-acetylated oligosaccharide(s) may be in a total amount of 0.35-0.56 g/100 g of composition, such as 0.35-0.52 g/100 g or 0.35-0.49 g/100 g. In a particular embodiment, the N-acetylated oligosaccharide(s) is/are in a total amount of 0.35 g/100 g of the composition. In another particular embodiment, the N-acetylated oligosaccharide(s) is/are in a total amount of 0.44 g/100 g of the composition.

Therefore in one embodiment of the present invention, the nutritional composition comprises at least one fucosylated oligosaccharide and at least one N-acetylated oligosaccharide wherein:
  the fucosylated oligosaccharide(s) is/are in a total amount of 0.8-1.5 g/L of the composition and/or in a total amount of 0.55-1.05 g/100 g of composition on a dry weight basis; and/or
  the N-acetylated oligosaccharide(s) is/are in a total amount of 0.5-0.8 g/L of the composition and/or in a total amount of 0.35-0.56 g/100 g of composition on a dry weight basis.

In another particular embodiment the nutritional composition of the present invention comprises at least one fucosylated oligosaccharide and at least one N-acetylated oligosaccharide wherein:
  the fucosylated oligosaccharide(s) is/are in a total amount of 0.85-1.3 g/L of the composition and/or in a total amount of 0.59-0.9 g/100 g of composition on a dry weight basis; and/or
  the N-acetylated oligosaccharide(s) is/are in a total amount of 0.5-0.75 g/L of the composition and/or in a total amount of 0.35-0.52 g/100 g of composition on a dry weight basis.

In another particular embodiment the nutritional composition of the present invention comprises at least one fucosylated oligosaccharide and at least one N-acetylated oligosaccharide wherein:
  the fucosylated oligosaccharide(s) is/are in a total amount of 1-1.25 g/L of the composition and/or in a total amount of 0.69-0.87 g/100 g of composition on a dry weight basis; and/or
  the N-acetylated oligosaccharide(s) is/are in a total amount of 0.5-0.7 g/L of the composition and/or in a total amount of 0.35-0.49 g/100 g of composition on a dry weight basis.

In another particular embodiment the nutritional composition of the present invention comprises at least one fucosylated oligosaccharide and at least one N-acetylated oligosaccharide wherein:
  the fucosylated oligosaccharide(s) is/are in a total amount of 1.05-1.25 g/L of the composition and/or in a total amount of 0.73-0.87 g/100 g of composition on a dry weight basis; and/or
  the N-acetylated oligosaccharide(s) is/are in a total amount of 0.5-0.7 g/L of the composition and/or in a total amount of 0.35-0.49 g/100 g of composition on a dry weight basis.

In a specific embodiment the nutritional composition according to the invention comprises at least one fucosylated oligosaccharide and at least one N-acetylated oligosaccharide wherein:
  the fucosylated oligosaccharide(s) is/are in a total amount of 1 g/L of the composition and/or in a total amount of 0.69 g/100 g of composition on a dry weight basis; and/or
  the N-acetylated oligosaccharide(s) is/are in a total amount of 0.5 g/L of the composition and/or in a total amount of 0.35 g/100 g of composition on a dry weight basis.

In another specific embodiment the nutritional composition according to the invention comprises at least one fucosylated oligosaccharide and at least one N-acetylated oligosaccharide wherein:
  the fucosylated oligosaccharide(s) is/are in a total amount of 1.24 g/L of the composition and/or in a total amount of 0.86 g/100 g of composition on a dry weight basis; and/or
  the N-acetylated oligosaccharide(s) is/are in a total amount of 0.63 g/L of the composition and/or in a total amount of 0.44 g/100 g of composition on a dry weight basis.

The fucosylated oligosaccharide(s) and the N-acetylated oligosaccharide(s) comprised in the nutritional composition according to the invention are typically present in a ratio fucosylated oligosaccharide(s):the N-acetylated oligosaccharide(s) of from 2:0.54 to 2:2.26, such as 2:0.76-2:1.8 or 2:0.8-2:1.4. In a particularly advantageous embodiment, this ratio is 2:1 or around 2:1.

The nutritional composition according to the present invention may also comprise at least another oligosaccharide(s) (i.e. other than the fucosylated oligosaccharide(s) and N-acetylated oligosaccharide(s) necessarily present in the composition) and/or at least a fiber(s) and/or at least a precursor(s) thereof. The other oligosaccharide and/or fiber and/or precursor thereof may be selected from the list comprising galacto-oligosaccharides (GOS), fructo-oligosaccharides (FOS), inulin, xylooligosaccharides (XOS), polydextrose, sialylated oligosaccharides, sialic acid, fucose and any combination thereof. They may be in an amount between 0 and 10% by weight of composition. In a particular embodiment, the nutritional composition can also contain at least one BMO (bovine milk oligosaccharide).

Suitable commercial products that can be used in addition to the oligosaccharides comprised in the oligosaccharide mixture to prepare the nutritional compositions according to the invention include combinations of FOS with inulin such as the product sold by BENEO under the trademark Orafti, or polydextrose sold by Tate & Lyle under the trademark STA-LITE®.

In a particular embodiment, the composition according to the invention can comprise sialylated oligosaccharide(s). There can be one or several sialylated oligosaccharide(s).

The sialylated oligosaccharide(s) can be selected from the group comprising 3' sialyllactose (3-SL), 6' sialyllactose (6-SL), and any combination thereof. In some embodiments of the invention the composition comprises 3-SL and 6-SL. In some particular embodiments the ratio between 3'-sialyllactose (3-SL) and 6'-sialyllactose (6-SL) can be in the range between 5:1 and 1:10, or from 3:1 and 1:1, or from 1:1 to 1:10. In some specific embodiments the sialylated oligosaccharide of the composition is 6' sialyllactose (6-SL).

The sialylated oligosaccharide(s) may be isolated by chromatographic or filtration technology from a natural source such as animal milks. Alternatively, they may be produced by biotechnological means using specific sialyltransferases or sialidases, neuraminidases, either by an enzyme based fermentation technology (recombinant or natural enzymes), by chemical synthesis or by a microbial fermentation technology. In the latter case microbes may either express their natural enzymes and substrates or may be engineered to produce respective substrates and enzymes. Single microbial cultures or mixed cultures may be used. Sialyl-oligosaccharide formation can be initiated by acceptor substrates starting from any degree of polymerisation (DP), from DP=1 onwards. Alternatively, sialyllactoses may be produced by chemical synthesis from lactose and free N'-acetylneuraminic acid (sialic acid). Sialyllactoses are also commercially available for example from Kyowa Hakko Kogyo of Japan.

In particular examples the composition may comprise from 0.05 to 5 g/L of sialylated oligosaccharide(s), or from 0.1 to 4 g/L, or from 0.3 to 2 g/L, or from 0.4 to 1.5 g/L, or from 0.4 to 1 g/L, for example 0.5 or 0.9 g/L of sialylated oligosaccharide(s). In some particular embodiments the composition can comprise from 0.8 to 1.7 g/l of sialylated oligosaccharide(s).

The composition according to the invention can contain from 0.03 to 3.5 g of sialylated oligosaccharide(s) per 100 g of composition on a dry weight basis, e.g. from 0.1 to 2 g or from 0.2 to 1 g or form 0.3 to 0.6 g of sialylated oligosaccharide(s) per 100 g of composition on a dry weight basis.

In some particular embodiments of the present invention, the nutritional composition comprises sialylated oligosaccharide(s) in an amount of below 0.1 g/100 g of composition on a dry weight basis.

In some particular embodiments of the present invention, the nutritional composition does not contain any sialylated oligosaccharide(s).

The composition according to the present invention may optionally also comprise at least one precursor of oligosaccharide. There can be one or several precursor(s) of oligosaccharide. For example the precursor of human milk oligosaccharide is sialic acid, fucose or a mixture thereof. In some particular embodiments the composition comprises sialic acid.

In particular examples the composition comprises from 0 to 3 g/L of precursor(s) of oligosaccharide, or from 0 to 2 g/L, or from 0 to 1 g/L, or from 0 to 0.7 g/L, or from 0 to 0.5 g/L or from 0 to 0.3 g/L, or from 0 to 0.2 g/L of precursor(s) of oligosaccharide.

The composition according to the invention can contain from 0 to 2.1 g of precursor(s) of oligosaccharide per 100 g of composition on a dry weight basis, e.g. from 0 to 1.5 g or from 0 to 0.8 g or from 0 to 0.15 g of precursor(s) of oligosaccharide per 100 g of composition on a dry weight basis.

The nutritional composition of the present invention can further comprise at least one probiotic (or probiotic strain), such as a probiotic bacterial strain.

The probiotic microorganisms most commonly used are principally bacteria and yeasts of the following genera: *Lactobacillus* spp., *Streptococcus* spp., *Enterococcus* spp., *Bifidobacterium* spp. and *Saccharomyces* spp.

In some particular embodiments, the probiotic is a probiotic bacterial strain. In some specific embodiments, it is particularly Bifidobacteria and/or Lactobacilli.

Suitable probiotic bacterial strains include *Lactobacillus rhamnosus* ATCC 53103 available from Valio Oy of Finland under the trademark LGG, *Lactobacillus rhamnosus* CGMCC 1.3724, *Lactobacillus paracasei* CNCM I-2116, *Lactobacillus johnsonii* CNCM I-1225, *Streptococcus salivarius* DSM 13084 sold by BLIS Technologies Limited of New Zealand under the designation KI2, *Bifidobacterium lactis* CNCM I-3446 sold inter alia by the Christian Hansen company of Denmark under the trademark Bb 12, *Bifidobacterium longum* ATCC BAA-999 sold by Morinaga Milk Industry Co. Ltd. of Japan under the trademark BB536, *Bifidobacterium breve* sold by Danisco under the trademark Bb-03, *Bifidobacterium breve* sold by Morinaga under the trade mark M-16V, *Bifidobacterium infantis* sold by Procter & Gamble Co. under the trademark Bifantis and *Bifidobacterium breve* sold by Institut Rosell (Lallemand) under the trademark R0070.

The nutritional composition according to the invention may contain from 10e3 to 10e12 cfu of probiotic strain, more preferably between 10e7 and 10e12 cfu such as between 10e8 and 1000 cfu of probiotic strain per g of composition on a dry weight basis.

In one embodiment the probiotics are viable. In another embodiment the probiotics are non-replicating or inactivated. There may be both viable probiotics and inactivated probiotics in some other embodiments.

The nutritional composition of the invention can further comprise at least one phage (bacteriophage) or a mixture of phages, preferably directed against pathogenic Streptococci, *Haemophilus, Moraxella* and Staphylococci.

The nutritional composition according to the invention can be for example an infant formula, a starter infant formula, a follow-on or follow-up formula, a baby food, an infant cereal composition, a fortifier such as a human milk fortifier, or a supplement. In some particular embodiments, the composition of the invention is an infant formula, a fortifier or a supplement that may be intended for the first 4 or 6 months of age. In a preferred embodiment the nutritional composition of the invention is an infant formula.

In some other embodiments the nutritional composition of the present invention is a fortifier. The fortifier can be a breast milk fortifier (e.g. a human milk fortifier) or a formula fortifier such as an infant formula fortifier or a follow-on/follow-up formula fortifier.

When the nutritional composition is a supplement, it can be provided in the form of unit doses.

The nutritional composition of the present invention can be in solid (e.g. powder), liquid or gelatinous form.

The nutritional composition according to the invention generally contains a protein source. The protein can be in an amount of from 1.6 to 3 g per 100 kcal. In some embodiments, especially when the composition is intended for premature infants, the protein amount can be between 2.4 and 4 g/100 kcal or more than 3.6 g/100 kcal. In some other embodiments the protein amount can be below 2.0 g per 100 kcal, e.g. between 1.8 to 2 g/100 kcal, or in an amount below 1.8 g per 100 kcal.

The type of protein is not believed to be critical to the present invention provided that the minimum requirements for essential amino acid content are met and satisfactory growth is ensured. Thus, protein sources based on whey, casein and mixtures thereof may be used as well as protein sources based on soy. As far as whey proteins are concerned, the protein source may be based on acid whey or sweet whey or mixtures thereof and may include alpha-lactalbumin and beta-lactoglobulin in any desired proportions.

In some advantageous embodiments the protein source is whey predominant (i.e. more than 50% of proteins are coming from whey proteins, such as 60% or 70%).

The proteins may be intact or hydrolysed or a mixture of intact and hydrolysed proteins. By the term "intact" is meant that the main part of the proteins are intact, i.e. the molecular structure is not altered, for example at least 80% of the proteins are not altered, such as at least 85% of the proteins are not altered, preferably at least 90% of the proteins are not altered, even more preferably at least 95% of the proteins are not altered, such as at least 98% of the proteins are not altered. In a particular embodiment, 100% of the proteins are not altered.

The term "hydrolysed" means in the context of the present invention a protein which has been hydrolysed or broken down into its component amino acids.

The proteins may be either fully or partially hydrolysed. It may be desirable to supply partially hydrolysed proteins (degree of hydrolysis between 2 and 20%), for example for infants or young children believed to be at risk of developing cow's milk allergy. If hydrolysed proteins are required, the hydrolysis process may be carried out as desired and as is known in the art. For example, whey protein hydrolysates may be prepared by enzymatically hydrolysing the whey fraction in one or more steps. If the whey fraction used as the starting material is substantially lactose free, it is found that the protein suffers much less lysine blockage during the hydrolysis process. This enables the extent of lysine blockage to be reduced from about 15% by weight of total lysine to less than about 10% by weight of lysine; for example about 7% by weight of lysine which greatly improves the nutritional quality of the protein source.

In an embodiment of the invention at least 70% of the proteins are hydrolysed, preferably at least 80% of the proteins are hydrolysed, such as at least 85% of the proteins are hydrolysed, even more preferably at least 90% of the proteins are hydrolysed, such as at least 95% of the proteins are hydrolysed, particularly at least 98% of the proteins are hydrolysed. In a particular embodiment, 100% of the proteins are hydrolysed.

In one particular embodiment the proteins of the nutritional composition are hydrolyzed, fully hydrolyzed or partially hydrolyzed. The degree of hydrolysis (DH) of the protein can be between 8 and 40, or between 20 and 60 or between 20 and 80 or more than 10, 20, 40, 60, 80 or 90.

In a particular embodiment the nutritional composition according to the invention is a hypoallergenic composition. In another particular embodiment the composition according to the invention is a hypoallergenic nutritional composition.

The nutritional composition according to the present invention generally contains a carbohydrate source. This is particularly preferable in the case where the nutritional composition of the invention is an infant formula. In this case, any carbohydrate source conventionally found in infant formulae such as lactose, sucrose, saccharose, maltodextrin, starch and mixtures thereof may be used although one of the preferred sources of carbohydrates is lactose.

The nutritional composition according to the present invention generally contains a source of lipids. This is particularly relevant if the nutritional composition of the invention is an infant formula. In this case, the lipid source may be any lipid or fat which is suitable for use in infant formulae. Some suitable fat sources include palm oil, high oleic sunflower oil and high oleic safflower oil. The essential fatty acids linoleic and α-linolenic acid may also be added, as well small amounts of oils containing high quantities of preformed arachidonic acid and docosahexaenoic acid such as fish oils or microbial oils. The fat source may have a ratio of n-6 to n-3 fatty acids of about 5:1 to about 15:1; for example about 8:1 to about 10:1.

The nutritional composition of the invention may also contain all vitamins and minerals understood to be essential in the daily diet and in nutritionally significant amounts. Minimum requirements have been established for certain vitamins and minerals. Examples of minerals, vitamins and other nutrients optionally present in the composition of the invention include vitamin A, vitamin B1, vitamin B2, vitamin B6, vitamin B12, vitamin E, vitamin K, vitamin C, vitamin D, folic acid, inositol, niacin, biotin, pantothenic acid, choline, calcium, phosphorous, iodine, iron, magnesium, copper, zinc, manganese, chlorine, potassium, sodium, selenium, chromium, molybdenum, taurine, and L-carnitine. Minerals are usually added in salt form. The presence and amounts of specific minerals and other vitamins will vary depending on the intended population.

If necessary, the nutritional composition of the invention may contain emulsifiers and stabilisers such as soy, lecithin, citric acid esters of mono- and diglycerides, and the like.

The nutritional composition of the invention may also contain other substances which may have a beneficial effect such as lactoferrin, nucleotides, nucleosides, and the like.

The nutritional composition of the invention may also contain carotenoid(s). In some particular embodiments of the invention, the nutritional composition of the invention does not comprise any carotenoid.

The nutritional composition according to the invention may be prepared in any suitable manner. A composition will now be described by way of example.

For example, a formula such as an infant formula may be prepared by blending together the protein source, the carbohydrate source and the fat source in appropriate proportions. If used, the emulsifiers may be included at this point. The vitamins and minerals may be added at this point but they are usually added later to avoid thermal degradation. Any lipophilic vitamins, emulsifiers and the like may be dissolved into the fat source prior to blending. Water, preferably water which has been subjected to reverse osmosis, may then be mixed in to form a liquid mixture. The temperature of the water is conveniently in the range between about 50° C. and about 80° C. to aid dispersal of the ingredients. Commercially available liquefiers may be used to form the liquid mixture.

The fucosylated oligosaccharide(s) and the N-acetylated oligosaccharide(s) may be added at this stage, especially if the final product is to have a liquid form. If the final product is to be a powder, they may likewise be added at this stage if desired.

The liquid mixture is then homogenised, for example in two stages.

The liquid mixture may then be thermally treated to reduce bacterial loads, by rapidly heating the liquid mixture to a temperature in the range between about 80° C. and about 150° C. for a duration between about 5 seconds and about 5 minutes, for example. This may be carried out by means of steam injection, an autoclave or a heat exchanger, for example a plate heat exchanger.

Then, the liquid mixture may be cooled to between about 60° C. and about 85° C. for example by flash cooling. The liquid mixture may then be again homogenised, for example in two stages between about 10 MPa and about 30 MPa in the first stage and between about 2 MPa and about 10 MPa in the second stage. The homogenised mixture may then be further cooled to add any heat sensitive components, such as vitamins and minerals. The pH and solids content of the homogenised mixture are conveniently adjusted at this point.

If the final product is to be a powder, the homogenised mixture is transferred to a suitable drying apparatus such as a spray dryer or freeze dryer and converted to powder. The powder should have a moisture content of less than about 5% by weight. The fucosylated oligosaccharide(s) and the N-acetylated oligosaccharide(s) may also or alternatively be added at this stage by dry-mixing or by blending them in a syrup form of crystals, along with the probiotic strain(s) (if used), and the mixture is spray-dried or freeze-dried.

If a liquid composition is preferred, the homogenised mixture may be sterilised then aseptically filled into suitable containers or may be first filled into the containers and then retorted.

In another embodiment, the composition of the invention may be a supplement.

The supplement may be in the form of tablets, capsules, pastilles or a liquid for example. The supplement may further contain protective hydrocolloids (such as gums, proteins, modified starches), binders, film forming agents, encapsulating agents/materials, wall/shell materials, matrix compounds, coatings, emulsifiers, surface active agents, solubilizing agents (oils, fats, waxes, lecithins etc.), adsorbents, carriers, fillers, co-compounds, dispersing agents, wetting agents, processing aids (solvents), flowing agents, taste masking agents, weighting agents, jellifying agents and gel forming agents. The supplement may also contain conventional pharmaceutical additives and adjuvants, excipients and diluents, including, but not limited to, water, gelatine of any origin, vegetable gums, lignin-sulfonate, talc, sugars, starch, gum arabic, vegetable oils, polyalkylene glycols, flavouring agents, preservatives, stabilizers, emulsifying agents, buffers, lubricants, colorants, wetting agents, fillers, and the like.

Further, the supplement may contain an organic or inorganic carrier material suitable for oral or parenteral administration as well as vitamins, minerals trace elements and other micronutrients in accordance with the recommendations of Government bodies such as the USRDA.

The nutritional composition according to the invention is for use in infants or young children. The infants or young children may be born term or preterm. In a particular embodiment the nutritional composition of the invention is for use in infants or young children that were born preterm. In a particular embodiment the nutritional composition of the invention is for use in preterm infants.

The nutritional composition of the present invention may also be used in an infant or a young child that was born by C-section or that was vaginally delivered. Indeed, as illustrated in the experimental part, the inventors of the present invention were able to show good results when administering the nutritional composition of the present invention to each of these populations.

In some embodiments the composition according to the invention can be for use before and/or during the weaning period.

The nutritional composition can be administered (or given or fed) at an age and for a period that depends on the needs. The nutritional composition of the present invention may be used for prevention or treatment purposes:

in preventing and/or treating infections and/or inflammations of the lower respiratory tract and/or of the ear in an infant or a young child;

in reducing fever in an infant or a young child;

in reducing the use of antibiotics in an infant or young child;

in reducing the use of antipyretics in an infant or young child; and/or in preventing and/or treating diseases/conditions involving fever and/or the administration of antibiotics or of antipyretics in an infant or a young child.

In some embodiments the nutritional composition is used for prevention purposes. The nutritional composition can be for example given immediately after birth of the infants. The composition of the invention can also be given during the first week of life of the infant, or during the first 2 weeks of life, or during the first 3 weeks of life, or during the first month of life, or during the first 2 months of life, or during the first 3 months of life, or during the first 4 months of life, or during the first 6 months of life, or during the first 8 months of life, or during the first 10 months of life, or during the first year of life, or during the first two years of life or even more. In some particularly advantageous embodiments of the invention, the nutritional composition is given (or administered) to an infant within the first 4 or 6 months of birth of said infant.

In some other embodiments, the nutritional composition of the invention is given few days (e.g. 1, 2, 3, 5, 10, 15, 20 . . . ), or few weeks (e.g. 1, 2, 3, 4, 5, 6, 7, 8, 9, 10 . . . ), or few months (e.g. 1, 2, 3, 4, 5, 6, 7, 8, 9, 10 . . . ) after birth. This may be especially the case when the infant is premature, but not necessarily.

In one embodiment the composition of the invention is given to the infant or young child as a supplementary composition to the mother's milk. In some embodiments the infant or young child receives the mother's milk during at least the first 2 weeks, first 1, 2, 4, or 6 months. In one embodiment the nutritional composition of the invention is given to the infant or young child after such period of mother's nutrition, or is given together with such period of mother's milk nutrition. In another embodiment the composition is given to the infant or young child as the sole or primary nutritional composition during at least one period of time, e.g. after the $1^{st}$, $2^{nd}$ or $4^{th}$ month of life, during at least 1, 2, 4 or 6 months.

In one embodiment the nutritional composition of the invention is a complete nutritional composition (fulfilling all or most of the nutritional needs of the subject). In another embodiment the nutrition composition is a supplement or a fortifier intended for example to supplement human milk or to supplement an infant formula or a follow-on/follow-up formula.

In some other embodiments the nutritional composition of the invention is given for treatment purposes. This will more be the case when the composition is used for the treatment of infections and/or inflammations of the lower respiratory tract and/or of the ear.

In these cases, the nutritional composition of the invention can be given for some days (1, 2, 3, 4, 5, 6 . . . ), or for some weeks (1, 2, 3, 4, 5, 6, 7, 8 or even more), or for some months (1, 2, 3, 4, 5, 6, 7, 8, 9, 10, 11 or even more), depending on the needs. It may be given once the symptoms appear or once these health diseases/conditions have been diagnosed. It may be given up to the symptoms of the treated diseases/conditions disappear, or several days/weeks/months after said disappearance.

The nutritional composition according to the invention may be used in preventing and/or treating infections and/or inflammations of the lower respiratory tract and/or of the ear. The infections and/or inflammations of the lower respiratory tract and/or of the ear may have a bacterial origin, a viral origin, or an environmental origin, as previously detailed. In some embodiments, these infections and/or inflammations have a bacterial origin. In some other embodiments, they have a viral origin.

The infections and/or inflammations of the lower respiratory tract may be for example pneumonia, bronchitis and/or bronchiolitis. They may be located in at least one of the following part of the lower respiratory tract: trachea, bronchi, bronchioles and/or lungs. In a particular example the nutritional composition according to the invention is used in preventing and/or treating bronchitis.

The infections and/or inflammations of the ear may be ear infections, ear inflammations, otitis, otitis media, acute otitis media. They may be located in the middle ear. In a particular example the nutritional composition according to the invention is used in preventing and/or treating otitis or otitis media.

The present inventors have also found that the particular nutritional composition according to the invention is particularly efficient in reducing fever and in reducing the use (i.e. administration) of antibiotics and of antipyretics in an infant or a young child. The nutritional composition according to the invention may also be used in reducing fever and/or in reducing the use of antibiotics and of antipyretics in the infant or young child in addition to the prevention and/or treatment of infections and/or inflammations of the lower respiratory tract and/or of the ear.

In a particular aspect, the present invention also refers to a nutritional composition comprising at least one fucosylated oligosaccharide and at least one N-acetylated oligosaccharide, for use in reducing fever and/or in reducing the administration of antibiotics and/or in reducing the use of antipyretics in an infant or a young child, wherein
    the fucosylated oligosaccharide(s) is/are in a total amount of 0.75-1.65 g/L of the composition and/or in a total amount of 0.52-1.15 g/100 g of composition on a dry weight basis; and
    the N-acetylated oligosaccharide(s) is/are in a total amount of 0.45-0.85 g/L of the composition and/or in a total amount of 0.31-0.59 g/100 g of composition on a dry weight basis.

The previously-mentioned embodiments and examples (e.g. related to the types and amounts of oligosaccharide, the nutritional composition, the administration, the targeted population . . . ) also apply for this aspect.

In another particular aspect, the present invention also refers to a nutritional composition comprising at least one fucosylated oligosaccharide and at least one N-acetylated oligosaccharide, for use in preventing and/or treating diseases/conditions (e.g. infections, inflammations . . . ) involving fever and/or the administration of antibiotics or of antipyretics in an infant or a young child, wherein
    the fucosylated oligosaccharide(s) is/are in a total amount of 0.75-1.65 g/L of the composition and/or in a total amount of 0.52-1.15 g/100 g of composition on a dry weight basis; and
    the N-acetylated oligosaccharide(s) is/are in a total amount of 0.45-0.85 g/L of the composition and/or in a total amount of 0.31-0.59 g/100 g of composition on a dry weight basis.

The previously-mentioned embodiments and examples (e.g. related to the types and amounts of oligosaccharide, the nutritional composition, the administration, the targeted population . . . ) also apply for this aspect.

Other Objects:

Another object of the present invention is the use of at least one fucosylated oligosaccharide and at least one N-acetylated oligosaccharide in the preparation of a nutritional composition for preventing and/or treating infections and/or inflammations of the lower respiratory tract and/or of the ear in an infant or young child, wherein
    the fucosylated oligosaccharide(s) is/are in a total amount of 0.75-1.65 g/L of the nutritional composition and/or in a total amount of 0.52-1.15 g/100 g of nutritional composition on a dry weight basis; and
    the N-acetylated oligosaccharide(s) is/are in a total amount of 0.45-0.85 g/L of the nutritional composition and/or in a total amount of 0.31-0.59 g/100 g of nutritional composition on a dry weight basis.

Another object of the present invention is the use of at least one fucosylated oligosaccharide and at least one N-acetylated oligosaccharide in the preparation of a nutritional composition for reducing fever and/or for reducing the administration of antibiotics and/or for reducing the administration of antipyretics and/or for preventing and/or treating diseases/conditions (e.g. infections, inflammations . . . ) involving fever and/or the administration of antibiotics or of antipyretics, in an infant or a young child, wherein
    the fucosylated oligosaccharide(s) is/are in a total amount of 0.75-1.65 g/L of the composition and/or in a total amount of 0.52-1.15 g/100 g of composition on a dry weight basis; and
    the N-acetylated oligosaccharide(s) is/are in a total amount of 0.45-0.85 g/L of the composition and/or in a total amount of 0.31-0.59 g/100 g of composition on a dry weight basis.

Another object of the present invention refers to the use of a nutritional composition comprising at least one fucosylated oligosaccharide and at least one N-acetylated oligosaccharide for reducing fever and/or for reducing the administration of antibiotics or of antipyretics in an infant or a young child, wherein
    the fucosylated oligosaccharide(s) is/are in a total amount of 0.75-1.65 g/L of the composition and/or in a total amount of 0.52-1.15 g/100 g of composition on a dry weight basis; and
    the N-acetylated oligosaccharide(s) is/are in a total amount of 0.45-0.85 g/L of the composition and/or in a total amount of 0.31-0.59 g/100 g of composition on a dry weight basis.

The previously-mentioned embodiments and examples (e.g. related to the types and amounts of oligosaccharide, the nutritional composition, the administration, the targeted population . . . ) also apply for these objects (i.e. uses).

Another object of the present invention is a pharmaceutical composition comprising at least one fucosylated oligosaccharide and at least one N-acetylated oligosaccharide for preventing and/or treating infections and/or inflammations of the lower respiratory tract and/or of the ear in an infant or young child, wherein
    the fucosylated oligosaccharide(s) is/are in a total amount of 0.75-1.65 g/L of the nutritional composition and/or in a total amount of 0.52-1.15 g/100 g of nutritional composition on a dry weight basis; and
    the N-acetylated oligosaccharide(s) is/are in a total amount of 0.45-0.85 g/L of the nutritional composition and/or in a total amount of 0.31-0.59 g/100 g of nutritional composition on a dry weight basis.

Another object of the present invention is a pharmaceutical composition comprising at least one fucosylated oligosaccharide and at least one N-acetylated oligosaccharide, for use in reducing fever and/or in reducing the administration of antibiotics and/or in reducing the administration of antipyretics in an infant or a young child, wherein
 the fucosylated oligosaccharide(s) is/are in a total amount of 0.75-1.65 g/L of the composition and/or in a total amount of 0.52-1.15 g/100 g of composition on a dry weight basis; and
 the N-acetylated oligosaccharide(s) is/are in a total amount of 0.45-0.85 g/L of the composition and/or in a total amount of 0.31-0.59 g/100 g of composition on a dry weight basis.

In another particular aspect, the present invention also refers to a pharmaceutical composition comprising at least one fucosylated oligosaccharide and at least one N-acetylated oligosaccharide, for use in preventing and/or treating diseases/conditions (e.g. infections, inflammations . . . ) involving fever and/or the administration of antibiotics and/or the administration of antipyretics in an infant or a young child, wherein
 the fucosylated oligosaccharide(s) is/are in a total amount of 0.75-1.65 g/L of the composition and/or in a total amount of 0.52-1.15 g/100 g of composition on a dry weight basis; and
 the N-acetylated oligosaccharide(s) is/are in a total amount of 0.45-0.85 g/L of the composition and/or in a total amount of 0.31-0.59 g/100 g of composition on a dry weight basis.

The previously-mentioned embodiments and examples (e.g. related to the types and amounts of oligosaccharide, the administration, the targeted population . . . ) also apply to these objects (i.e. pharmaceutical composition).

Another object of the present invention refers to a method for preventing and/or treating infections and/or inflammations of the lower respiratory tract and/or of the ear in an infant or a young child, said method comprising administering to said infant or young child a nutritional composition comprising at least one fucosylated oligosaccharide and at least one N-acetylated oligosaccharide, wherein
 the fucosylated oligosaccharide(s) is/are in a total amount of 0.75-1.65 g/L of the nutritional composition and/or in a total amount of 0.52-1.15 g/100 g of nutritional composition on a dry weight basis; and
 the N-acetylated oligosaccharide(s) is/are in a total amount of 0.45-0.85 g/L of the nutritional composition and/or in a total amount of 0.31-0.59 g/100 g of nutritional composition on a dry weight basis.

Another object of the present invention is a method for reducing fever and/or for reducing the administration of antibiotics and/or for reducing the administration of antipyretics and/or for preventing and/or treating diseases/conditions (e.g. infections, inflammations . . . ) involving fever and/or the administration of antibiotics in an infant or a young child, said method comprising administering to said infant or young child a nutritional composition comprising at least one fucosylated oligosaccharide and at least one N-acetylated oligosaccharide, wherein
 the fucosylated oligosaccharide(s) is/are in a total amount of 0.75-1.65 g/L of the nutritional composition and/or in a total amount of 0.52-1.15 g/100 g of nutritional composition on a dry weight basis; and
 the N-acetylated oligosaccharide(s) is/are in a total amount of 0.45-0.85 g/L of the nutritional composition and/or in a total amount of 0.31-0.59 g/100 g of nutritional composition on a dry weight basis.

The different embodiments, details and examples previously described in the specification (e.g. related to the types and amounts of oligosaccharide, the nutritional composition, the administration, the targeted population . . . ) also apply to these objects (i.e. methods).

EXAMPLES

The following examples illustrate some specific embodiments of the composition for use according to the present invention. The examples are given solely for the purpose of illustration and are not to be construed as limitations of the present invention.

Example 1

An example of the composition of a nutritional composition (e.g. an infant formula) according to the present invention is given in the below table 1. This composition is given by way of illustration only.

TABLE 1 an example of the composition of a nutritional composition (e.g. an infant formula) according to the present invention

| Nutrients | | per 100 kcal | per litre |
|---|---|---|---|
| Energy (kcal) | | 100 | 670 |
| Protein (g) | | 1.83 | 12.3 |
| Fat (g) | | 5.3 | 35.7 |
| Linoleic acid (g) | | 0.79 | 5.3 |
| α-Linolenic acid (mg) | | 101 | 675 |
| Lactose (g) | | 11.2 | 74.7 |
| Minerals (g) | | 0.37 | 2.5 |
| Na (mg) | | 23 | 150 |
| K (mg) | | 89 | 590 |
| Cl (mg) | | 64 | 430 |
| Ca (mg) | | 62 | 410 |
| P (mg) | | 31 | 210 |
| Mg (mg) | | 7 | 50 |
| Mn (μg) | | 8 | 50 |
| Se (μg) | | 2 | 13 |
| Vitamin A (μg RE) | | 105 | 700 |
| Vitamin D (μg) | | 1.5 | 10 |
| Vitamin E (mg TE) | | 0.8 | 5.4 |
| Vitamin K1 (μg) | | 8 | 54 |
| Vitamin C (mg) | | 10 | 67 |
| Vitamin B1 (mg) | | 0.07 | 0.47 |
| Vitamin B2 (mg) | | 0.15 | 1.0 |
| Niacin (mg) | | 1 | 6.7 |
| Vitamin B6 (mg) | | 0.075 | 0.50 |
| Folic acid (μg) | | 9 | 60 |
| Pantothenic acid (mg) | | 0.45 | 3 |
| Vitamin B12 (μg) | | 0.3 | 2 |
| Biotin (μg) | | 2.2 | 15 |
| Choline (mg) | | 10 | 67 |
| Fe (mg) | | 1.2 | 8 |
| I (μg) | | 15 | 100 |
| Cu (mg) | | 0.06 | 0.4 |
| Zn (mg) | | 0.75 | 5 |
| Oligosaccharides | 2FL (g) | 0.15 | 1 |
| (HMOs) | LNnT (g) | 0.075 | 0.5 |

Example 2

Description of the Study
A controlled, single-blind, randomized, multi-center, interventional clinical trial of 2 groups in parallel was made. Infants were recruited and randomized to one of the 2 study arms within 14 days after birth. The study arms consisted of a classical infant starter formula without HMO [Control] or this classical infant starter formula supplemented with 2 HMOs [HMO].

The composition of the tested infant formula with or without the addition of HMOs was equivalent to the composition shown in table 1, except that:
- the control infant formula contained no oligosaccharides/HMOs (i.e. no 2' Fucosyllactose and no lacto-N-neotetraose);
- the tested infant formula with HMOs contained 2' Fucosyllactose but in an amount of 1.24 g/L (corresponding to an amount of 0.86 g/100 g powder before reconstitution; reconstitution was 129.18 g powder/900 mL) and also lacto-N-neotetraose but in an amount of 0.63 g/L (corresponding to 0.44 g/100 g powder before reconstitution; reconstitution was 129.18 g powder/900 mL).

Introduction of weaning food was from 4 months onwards.

The study consists of a 6 months±7 days treatment period with one of the two treatments and a 6 months follow-up period without treatment.

Findings

The inventors surprisingly observed that infants of the HMO group (i.e. those fed a classical formula supplemented with 1.24 g/L of 2'-fucosyllactose and 0.63 g/L lacto-N-neotetraose had less bronchitis (FIG. 1). Depicted are number of infants with at least one event.

The inventors also surprisingly observed that the infants of the HMO group tended to have less ear infections/inflammations (FIG. 2). Depicted are number of infants with at least one event. The registered ear infections/inflammations encompass any ear infections, ear inflammations, otitis, otitis media, acute otitis media, otitis externa, mastoiditis or labyrinthitis diagnosed by a doctor or a health care practitioner.

The inventors also surprisingly observed that the infants of the HMO group needed less antibiotics (FIG. 3) and had less fever (FIG. 4).

These effects were observed independently of the mode of delivery.

Evaluation of the number of incidences per group confirms the above described findings (FIGS. 5 and 6). Notably, the infants who got the test formula with HMO had a lower number of events for (i) bronchitis (FIGS. 5A and 6A), (ii) ear infection/inflammation (FIGS. 5B and 6B), (iii) antibiotic use (FIGS. 5C and 6C) and (iv) antipyretic use (FIGS. 5D and 6D).

All these results were observed during the entire length of the experiment (12 month-period), e.g. from 0 to 4 months, from 0 to 6 months and from 0 to 12 months.

A composition comprising at least one fucosylated oligosaccharide and at least one N-acetylated oligosaccharide in the claimed amounts is therefore very efficient in infants for use in preventing and/or treating infections and/or inflammations of the lower respiratory tract and of the ear but also in reducing fever and in reducing the administration of antibiotics and of antipyretics in said infants.

The invention claimed is:

1. A method for reducing an incidence and/or severity of and/or treating an infection and/or inflammation of the lower respiratory tract and/or of the ear selected from the group consisting of pneumonia, bronchitis, bronchiolitis, otitis, otitis media and combinations thereof in an infant or a young child in need thereof, the method comprising administering to the infant or young child a nutritional composition comprising 2'-fucosyllactose (2'FL) as the only fucosylated oligosaccharide in the nutritional composition in a total amount of 0.85-1.3 g/L of the nutritional composition and/or in a total amount of 0.59-0.9 g/100 g of the nutritional composition on a dry weight basis; and lacto-N-neotetraose (LNnT) as the only N-acetylated oligosaccharide in the nutritional composition in a total amount of 0.45-0.75 g/L of the composition and/or in a total amount of 0.35-0.52 g/100 g of the nutritional composition on a dry weight basis, wherein the nutritional composition does not contain any sialylated oligosaccharide.

2. The method according to claim 1, wherein the nutritional composition comprises at least another ingredient selected from the group consisting of galacto-oligosaccharides, fructo-oligosaccharides, xylooligosaccharides, inulin, polydextrose, sialic acid, fucose and combinations thereof.

3. The method according to claim 1, wherein the nutritional composition further comprises at least one probiotic in an amount of from $10^3$ to $10^{12}$ cfu/g of the nutritional composition (dry weight).

4. The method according to claim 1, wherein the nutritional composition is in a form selected from the group consisting of an infant formula, a starter infant formula, a follow-on or follow-up infant formula, a baby food, an infant cereal composition, a fortifier and a supplement.

5. The method according to claim 1, wherein the infection and/or inflammation of the lower respiratory tract and/or of the ear has an origin selected from the group consisting of a bacterial origin, a viral origin, and an environmental origin.

6. The method according to claim 1, wherein the 2'-fucosyllactose (2'FL) and the lacto-N-neotetraose (LNnT) are the only HMOs in the nutritional composition.

7. The method according to claim 1, wherein the infant or the young child was born by C-section.

* * * * *